(12) United States Patent
Sakaguchi et al.

(10) Patent No.: US 11,123,521 B2
(45) Date of Patent: Sep. 21, 2021

(54) CATHETER

(71) Applicant: TERUMO KABUSHIKI KAISHA, Tokyo (JP)

(72) Inventors: Yuuki Sakaguchi, Fujinomiyua (JP); Tomohito Koketsu, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 541 days.

(21) Appl. No.: 15/872,250

(22) Filed: Jan. 16, 2018

(65) Prior Publication Data

US 2018/0214120 A1 Aug. 2, 2018

(30) Foreign Application Priority Data

Jan. 31, 2017 (JP) .............................. JP2017-015611

(51) Int. Cl.
A61M 39/10 (2006.01)
A61M 25/01 (2006.01)
A61B 34/00 (2016.01)
A61M 25/00 (2006.01)
A61B 8/12 (2006.01)
(Continued)

(52) U.S. Cl.
CPC ......... A61M 25/0105 (2013.01); A61B 34/00 (2016.02); A61M 25/00 (2013.01); A61B 8/12 (2013.01); A61B 8/445 (2013.01); A61M 25/0108 (2013.01); A61M 25/0662 (2013.01); A61M 25/09041 (2013.01); A61M 39/10 (2013.01); A61M 2025/0183 (2013.01); A61M 2025/0681 (2013.01); A61M 2039/1038 (2013.01)

(58) Field of Classification Search
CPC .............. A61M 39/10; A61M 39/1011; A61M 2039/1016; A61M 2039/1027; A61M 2039/1066; A61M 39/1055; A61M 25/0097; A61M 25/01; A61M 25/0105
See application file for complete search history.

(56) References Cited

U.S. PATENT DOCUMENTS

2011/0077621 A1* 3/2011 Graham ................ A61M 25/01
604/528
2013/0282007 A1 10/2013 Chong et al.
(Continued)

FOREIGN PATENT DOCUMENTS

JP 2000-147390 A 5/2000
JP 2001-046378 A 2/2001
(Continued)

OTHER PUBLICATIONS

Office Action (Notice of Reasons for Refusal) dated Feb. 25, 2020, by the Japanese Patent Office in corresponding Japanese Patent Application No. 2017-015611 and an English Translation of the Office Action. (6 pages).

Primary Examiner — Emily L Schmidt
(74) Attorney, Agent, or Firm — Buchanan Ingersoll & Rooney PC

(57) ABSTRACT

A catheter includes a sheath configured to be inserted into a body lumen, a drive shaft configured to be inserted into the sheath and to transmit mechanical drive force, an operation unit configured to operate the drive shaft, and a connection section having a proximal side connected to the operation unit and a distal side connected to the sheath in such a way as to be attachable to and detachable from the sheath.

19 Claims, 14 Drawing Sheets

(51) Int. Cl.
    *A61M 25/09*     (2006.01)
    *A61M 25/06*     (2006.01)
    *A61B 8/00*     (2006.01)

(56) References Cited

U.S. PATENT DOCUMENTS

2016/0143616 A1    5/2016    Okubo et al.
2017/0000999 A1*    1/2017    Dennis ............... A61M 39/1011

FOREIGN PATENT DOCUMENTS

| | | |
|---|---|---|
| JP | 2002-125978 A | 5/2002 |
| JP | 2014-508556 A | 4/2014 |
| JP | 2016-000124 A | 1/2016 |
| WO | WO 2014/188969 A1 | 11/2014 |

\* cited by examiner

CATHETER

CROSS-REFERENCE TO RELATED APPLICATION

This application claims priority to Japanese Application No. 2017-015611 filed on Jan. 31, 2017, the entire content of which is incorporated herein by reference.

TECHNICAL FIELD

The present invention relates to a catheter.

BACKGROUND ART

Heretofore, in order to diagnose or treat a target lesion in a body lumen such as a blood vessel, a catheter is used which is equipped with a drive shaft which transmits mechanical drive force, such as a diagnostic imaging catheter. Such a catheter includes a sheath, which is configured to be inserted into a body lumen, a drive shaft, which is inserted into the sheath and transmits mechanical drive force, and an operation unit, which is connected to the sheath and used to operate the drive shaft.

When such a catheter is inserted into the body lumen, an immovable state in which the catheter gets held or wedged with, for example, a stent placed in the body lumen or a stenosed site in the body lumen may occur, so that the catheter may in some cases become difficult to extract from inside the body lumen. In such cases, an operation is usually performed which improves the operability of a distal portion of the sheath by extracting the drive shaft from inside the sheath and, instead, inserting a guide wire which is higher in rigidity than the drive shaft and which then resolves the immovable state.

For example, a catheter discussed in PCT Publication No. WO/2014/188969 is equipped with a connection section which allows connection and disconnection at the midway portion of an operation unit. Disconnection of the connection section enables separating a part of the operation unit and extracting the drive shaft from inside the sheath.

In a case where even the insertion of a guide wire higher in rigidity in place of the drive shaft into the sheath, as mentioned above, is not able to resolve the immovable state, an operation is usually performed which resolves the immovable state by inserting a guiding catheter into the body lumen while causing the sheath to be inserted therethrough into the guiding catheter. However, in the catheter discussed in the above-mentioned PCT Publication No. WO/2014/188969, since a part of the operation unit is in a state of being connected to the sheath, it is impossible to cause the sheath to be inserted through into the guiding catheter. Therefore, to disconnect the part of the operation unit from the sheath, it is necessary to cut off a proximal portion of the sheath. With this, in spite of an emergency situation, an operation of preparing a cutting tool, such as a skin cut scalpel, to resolve the immovable state and cutting the sheath would be required, so that a prompt procedure may be hindered.

Furthermore, the sheath has a small wall thickness and, therefore, may be damaged if being reused, and, since the sheath is inserted into the body lumen and directly contacts a body fluid, the sheath is also required to be made disposable from a hygiene viewpoint. On the other hand, the drive shaft and the operation unit, which is not inserted into the body lumen, can be reused after being subjected to appropriate treatments, such as sterilization and disinfection, as carried out in, for example, an endoscope. However, in the catheter discussed in the above-mentioned PCT Publication No. WO/2014/188969, since a part of the operation unit is in a state of being connected to the sheath, the operation unit is also required to be made disposable. Since the operation unit cannot be reused, a decrease in medical economic performance may be caused.

SUMMARY

The disclosure herein provides a catheter which enables a prompt procedure and is capable of contributing to medical economic performance by configuring an operation unit in such a way as to be attachable to and detachable from a sheath.

According to the disclosure, a catheter includes a sheath configured to be inserted into a body lumen, a drive shaft configured to be inserted into the sheath and to transmit mechanical drive force, an operation unit configured to operate the drive shaft, and a connection section having a proximal side connected to the operation unit and a distal side connected to the sheath in such a way as to be attachable to and detachable from the sheath.

With such a catheter configured as described above, when the catheter gets stuck or wedged in the body lumen, detaching the connection section from the sheath enables separating the sheath from the connection section and the operation unit. This enables performing an operation which improves the operability of a distal portion of the sheath by extracting the drive shaft from inside the sheath and, instead, inserting a guide wire which is higher in rigidity than the drive shaft and then resolves the immovable state. Furthermore, separating the sheath from the connection section and the operation unit causes only the sheath to remain in the living body and, therefore, enables promptly performing an operation which resolves the immovable state by inserting a guiding catheter into the body lumen while causing the sheath to be inserted through into the guiding catheter without cutting off a proximal portion of the sheath. Moreover, since the sheath, which is inserted into the body lumen and directly contacts a body fluid, can be separated from the connection section and the operation unit, which are not inserted into the body lumen, only the sheath can be made disposable and the drive shaft, the connection section, and the operation unit can be reused. This reduces components to be disposed of in the catheter and, therefore, enables improving medical economic performance.

BRIEF DESCRIPTION OF THE DRAWINGS

FIGS. 4(A) and 4(B) are diagrams illustrating a pullback operation (an inward pulling operation), in which FIG. 4(A) is a side view of the diagnostic imaging catheter before the pullback operation is performed and FIG. 4(B) is a side view of the catheter when the pullback operation is being performed.

FIGS. 8(A) and 8(B) are top views of the connection section, in which FIG. 8(A) illustrates the engagement state and FIG. 8(B) illustrates the disengagement state, in which the engagement portion is disengaged from the engaged portion.

DETAILED DESCRIPTION

Figure 1:
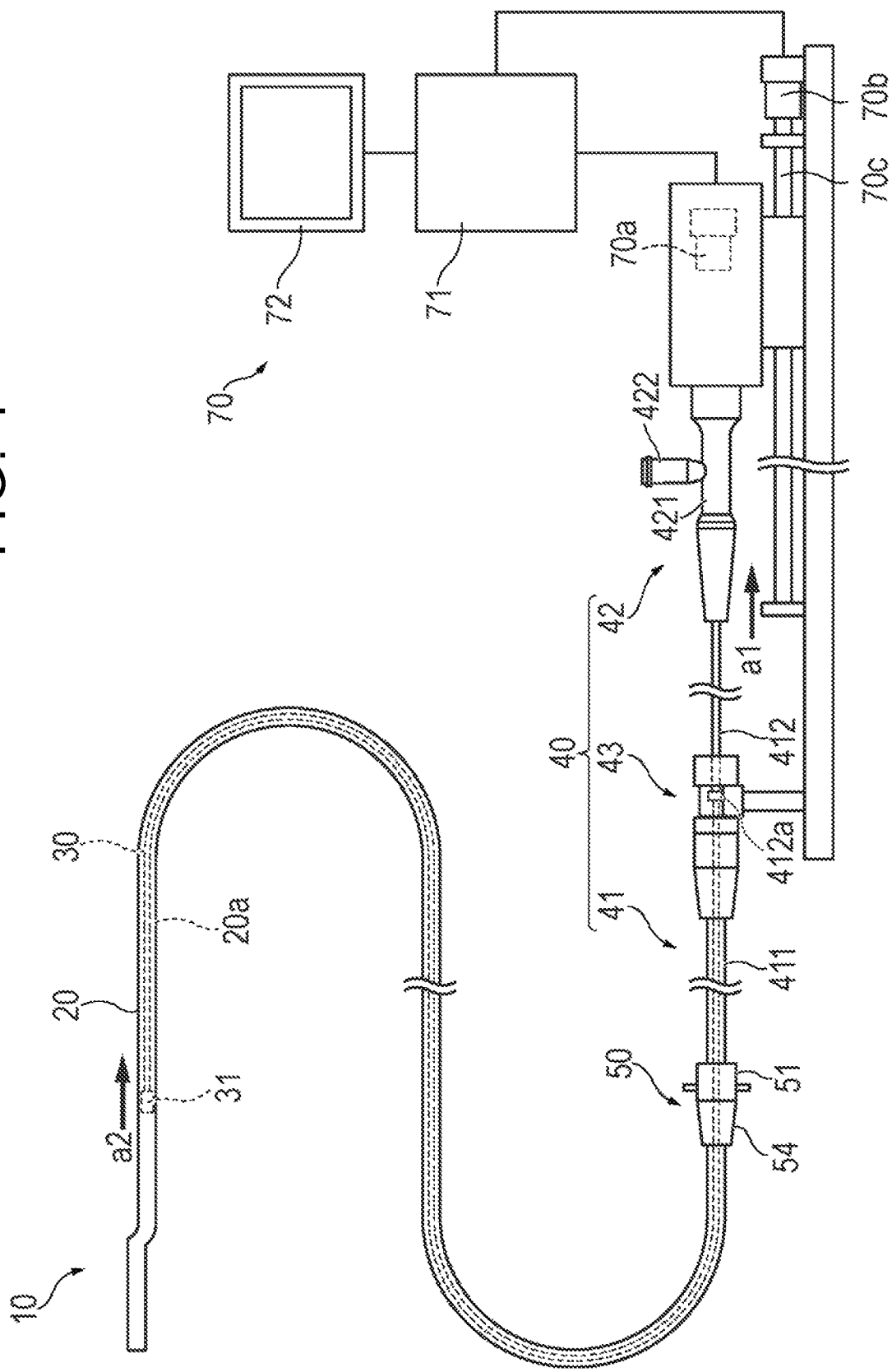
FIG. 1 is a plan view illustrating a state in which an external apparatus is connected to a catheter according to a first exemplary embodiment of the disclosure.

Hereinafter, embodiments of the invention will be described with reference to the accompanying drawings. Furthermore, the following description should not be construed to limit the technical scope set forth in the claims or the meanings of terms. Moreover, dimensional ratios illustrated in the drawings are exaggerated for the purpose of illustration and may be different from the actual ratios.

Figure 2:
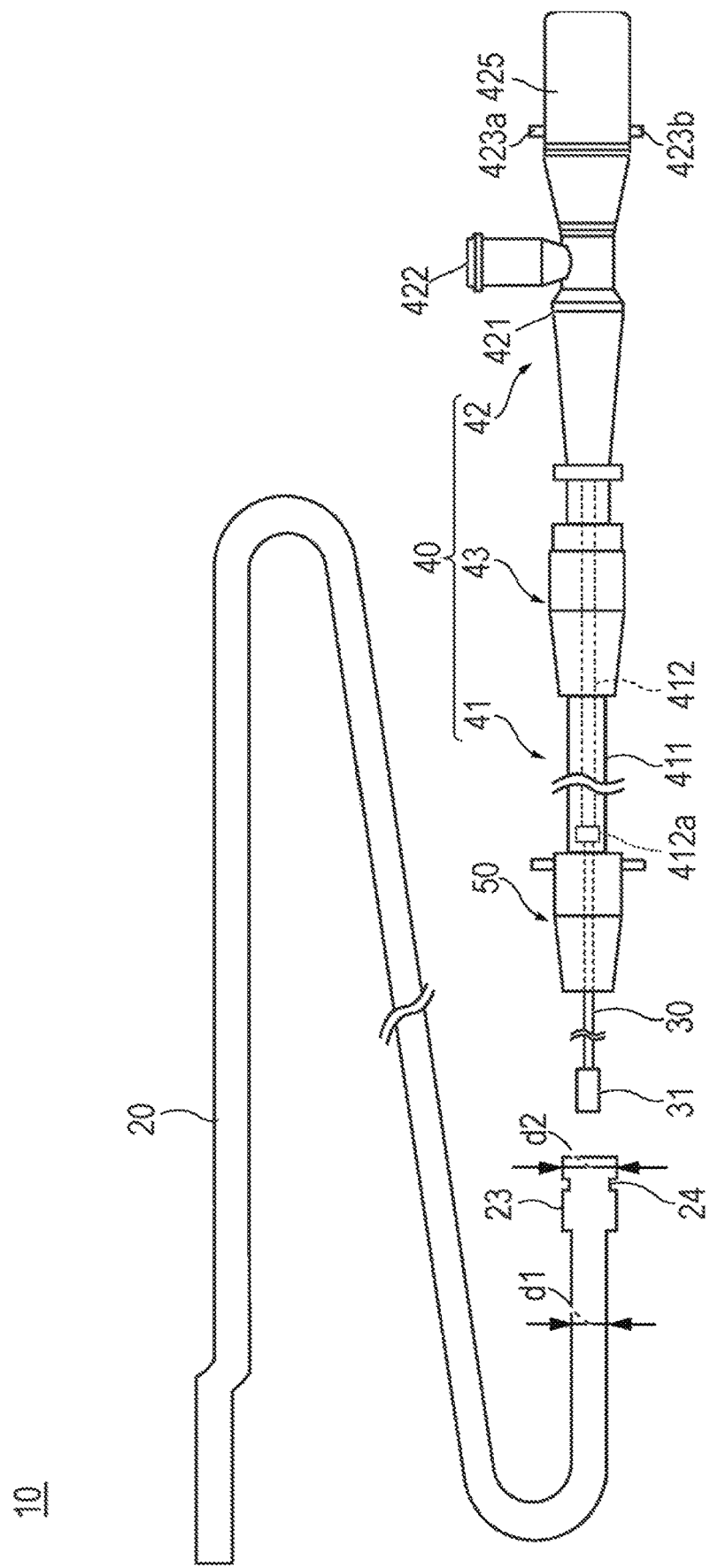
FIG. 2 is a plan view illustrating a state in which a connection section of the catheter according to the first exemplary embodiment is detached from a sheath.
Figure 3A:
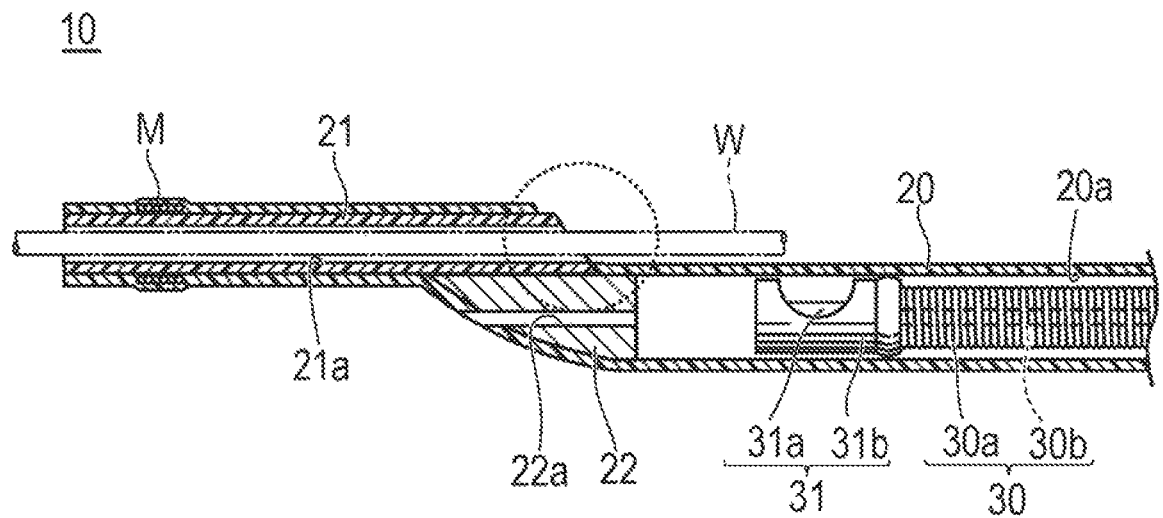
FIG. 3(A) is an enlarged sectional view illustrating a configuration of a distal side of the catheter.
Figure 3B:
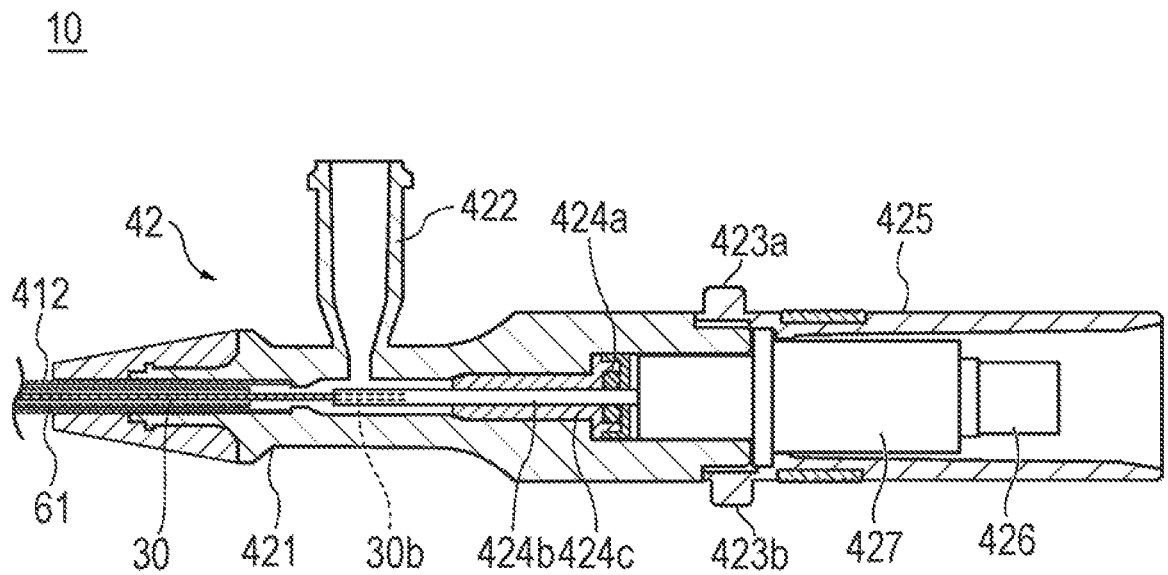
FIG. 3(B) is an enlarged sectional view illustrating a configuration of a proximal side of the catheter.
Figure 4A:
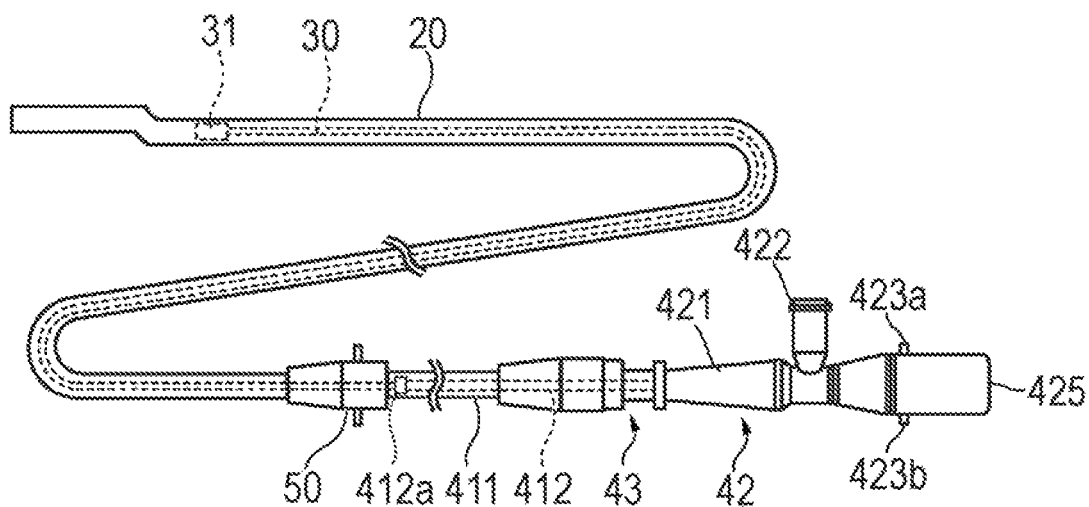
Figure 4B:
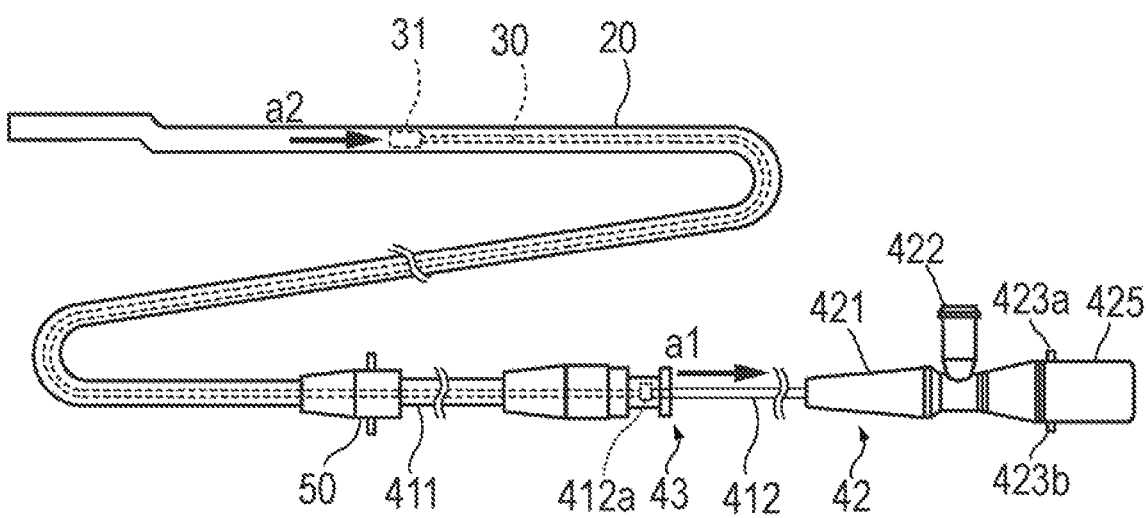
Figure 5:
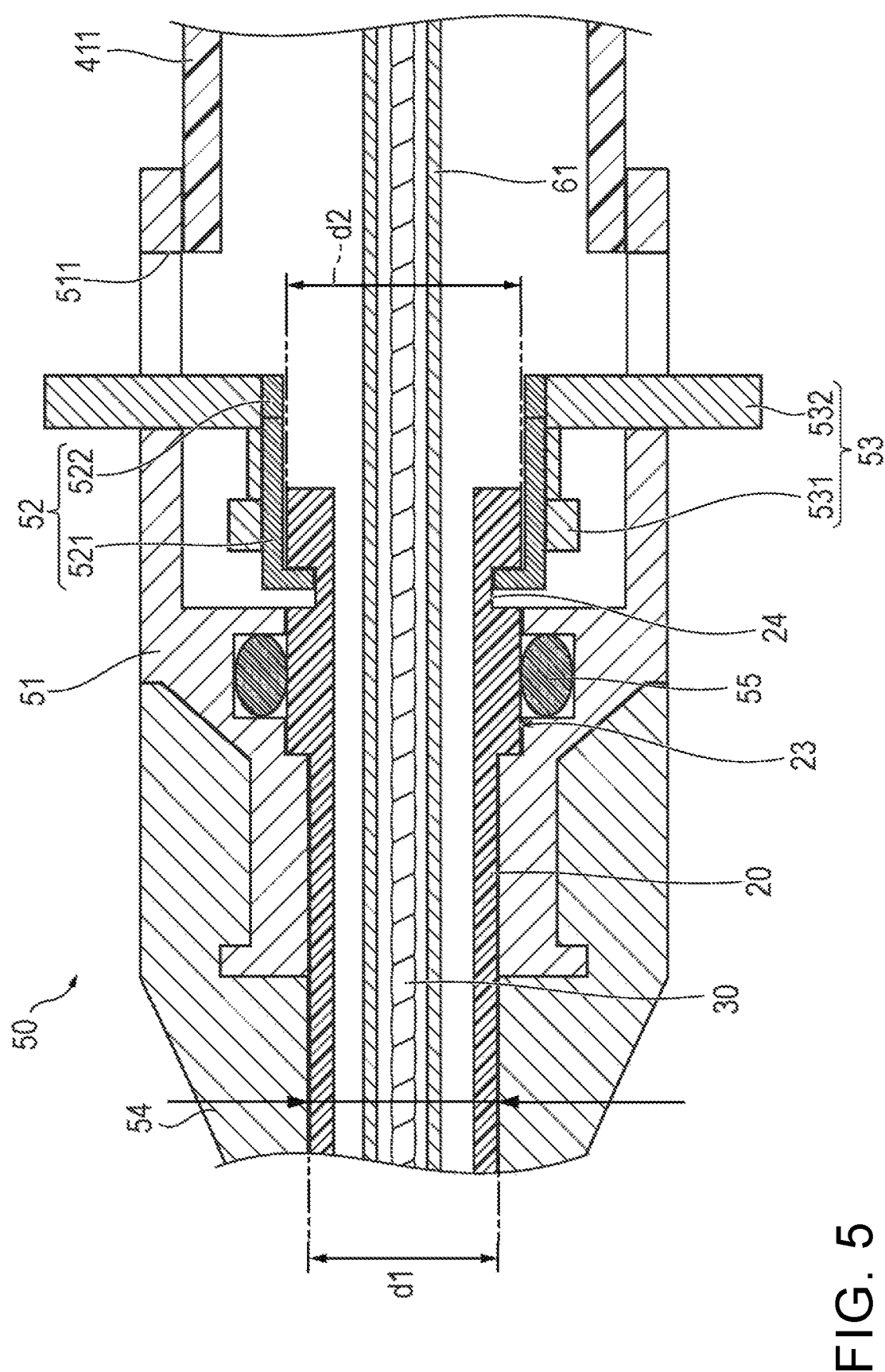
FIG. 5 is an enlarged sectional view illustrating a configuration of a portion near the connection section and illustrates an engagement state in which an engagement portion is engaged with an engaged portion.
Figure 6:
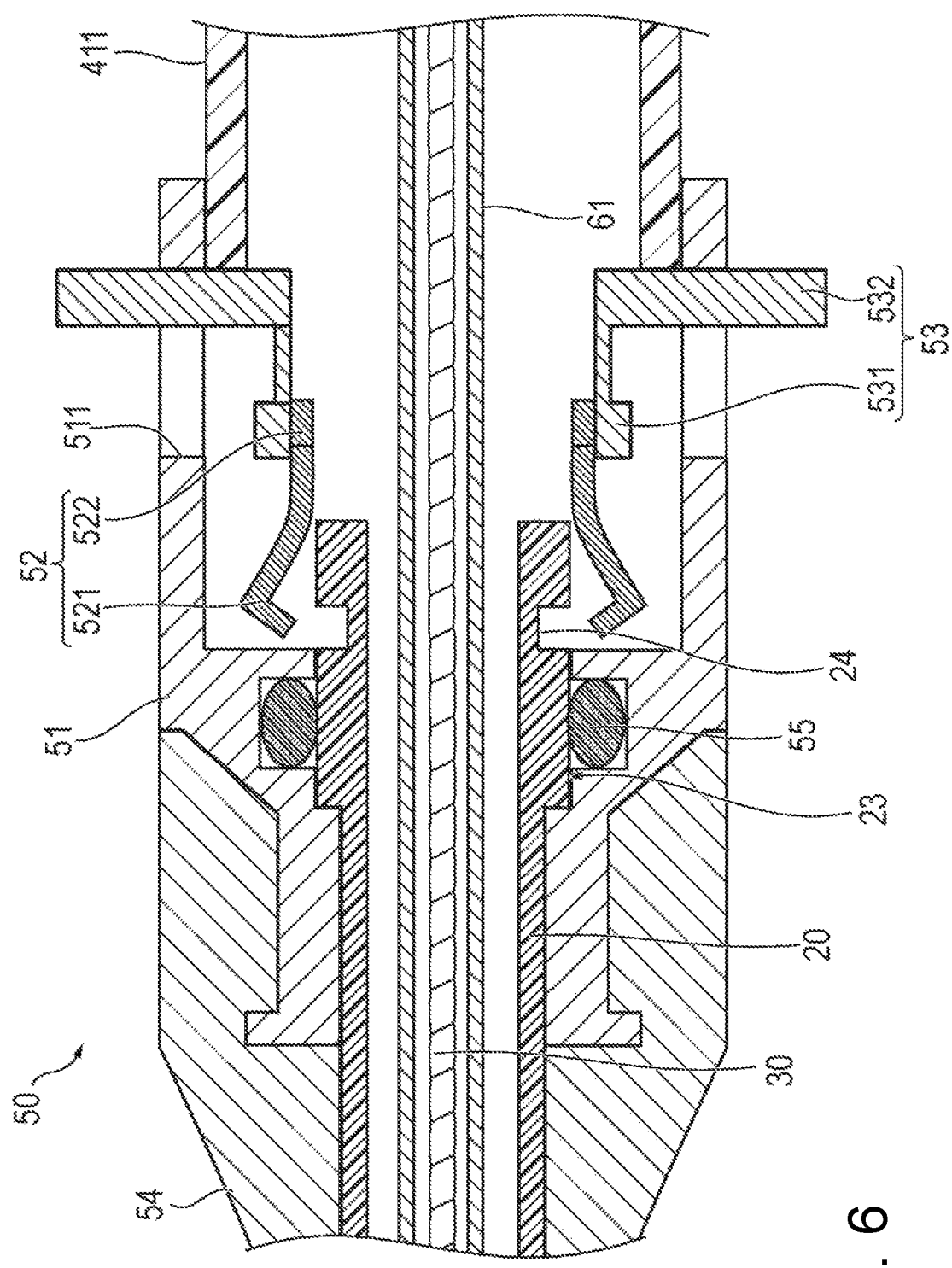
FIG. 6 is an enlarged sectional view illustrating a configuration of the portion near the connection section and illustrates a disengagement state in which the engagement portion is disengaged from the engaged portion.
Figure 7A:
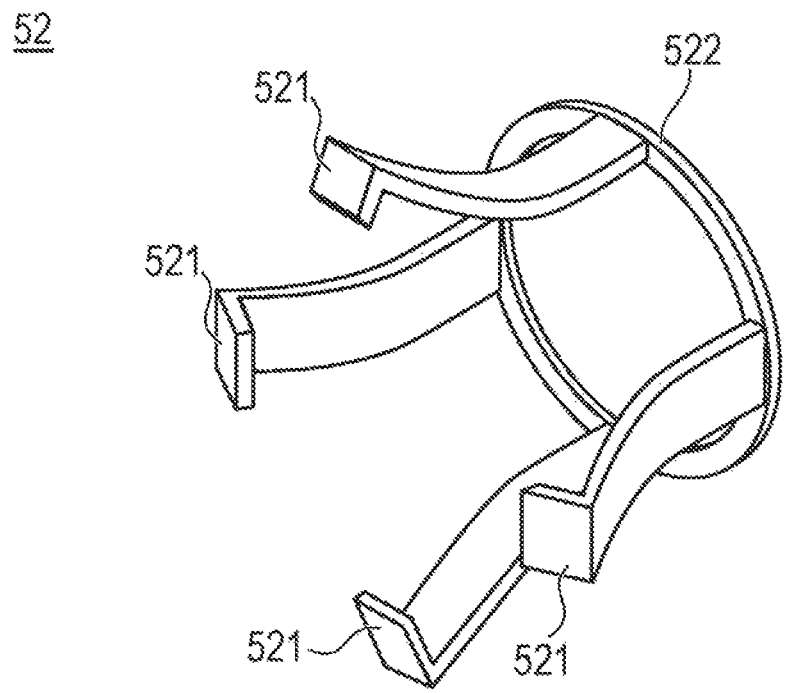
FIG. 7(A) is a perspective view of the engagement portion.
Figure 7B:
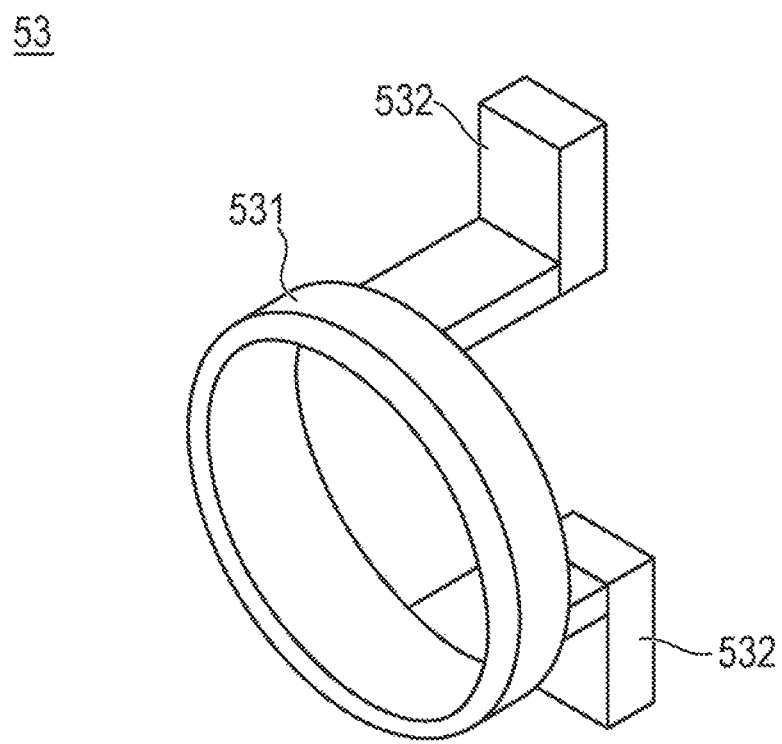
FIG. 7(B) is a perspective view of a switching portion.
Figure 8A:
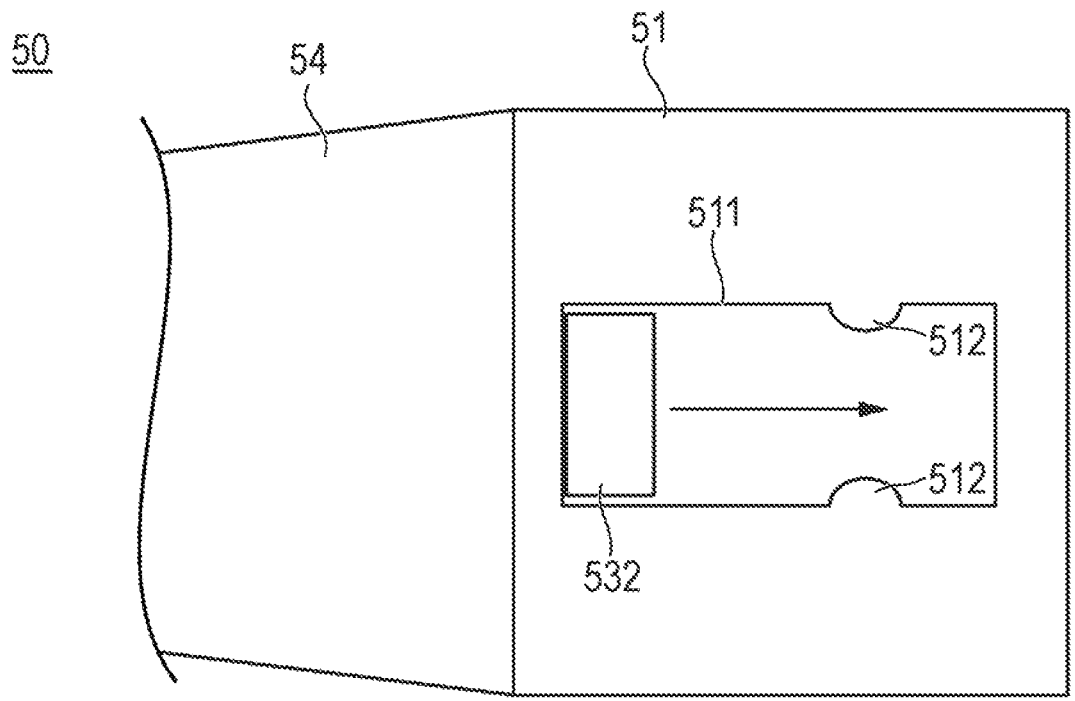
Figure 8B:
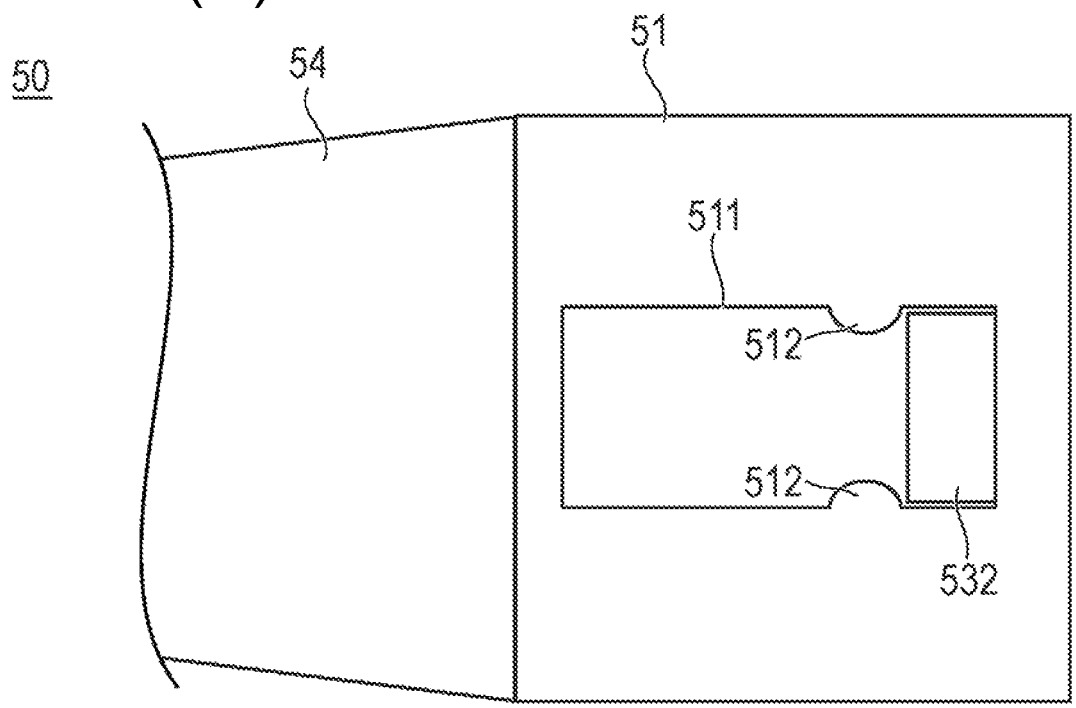

FIG. 1 is a plan view illustrating a state in which an external drive apparatus 70 is connected to a catheter 10 according to a first exemplary embodiment, FIG. 2 is a plan view illustrating a state in which a connection section 50 of the catheter 10 is detached from a sheath 20, FIGS. 3(A) and 3(B) are diagrams illustrating configurations of various portions of the catheter 10 according to the first exemplary embodiment, FIGS. 4(A) and 4(B) are diagrams illustrating a pullback operation, FIG. 5 and FIG. 6 are enlarged sectional views illustrating a configuration of a portion near the connection section 50 according to the first exemplary embodiment, FIG. 7(A) is a perspective view of an engagement portion 52, FIG. 7(B) is a perspective view of a switching portion 53, and FIGS. 8(A) and 8(B) are top views of the connection section 50.

The catheter 10 according to the first exemplary embodiment of the disclosure is a diagnostic imaging catheter which is configured to be inserted mainly into a body lumen to acquire a diagnostic image using ultrasound waves so as to diagnose a target lesion in the body lumen. As illustrated in FIG. 1, the catheter 10 is used in a state of being connected to an external drive apparatus 70, which drives the catheter 10.

As illustrated in FIG. 1, the catheter 10 includes, in broad terms, a sheath 20, which is configured to be inserted into the body lumen, a drive shaft 30, which has a distal portion at which a transmitting and receiving unit 31 that transmits and receives ultrasound waves is mounted, an operation unit 40, which is provided at the proximal side of the sheath 20 and configured to operate the drive shaft 30, and a connection section 50 having a proximal side connected to the operation unit 40 and a distal side connected to the sheath 20 in such a way as to be attachable to and detachable from the sheath 20.

Furthermore, in the context of the present disclosure, a side of the catheter 10 which is inserted into the body lumen is referred to as a distal end or a distal side, a side at which the catheter 10 is connected to the external drive apparatus 70 is referred to as a proximal end or a proximal side, and an extending direction of the sheath 20 is referred to as an axial direction.

As illustrated in FIG. 2, the catheter 10 is configured in such a manner that the drive shaft 30, the operation unit 40, and the connection section 50 can be separated from the sheath 20 by detaching the connection section 50 from the sheath 20. This enables detaching only the sheath 20.

Hereinafter, configurations of various portions of the catheter 10 are described in detail.

The sheath 20 is equipped with a lumen 20a, into which the drive shaft 30 is inserted in such a way as to be movable forward and backward. The sheath 20 is formed of a material having a high ultrasound transmissivity. The range of area where the transmitting and receiving unit 31 is moved in the axial direction of the sheath 20 defines an acoustic window portion having ultrasound transmissivity higher than those of other portions.

As illustrated in FIG. 3(A), the catheter 10 according to the first exemplary embodiment is configured as what is called a "rapid exchange (RX) type" in which a guide wire insertion member 21, which is equipped with a guide wire lumen 21a into which a guide wire W is able to be inserted through, is attached to a distal portion of the sheath 20 in such a way as to be arranged in parallel with the lumen 20a provided in the sheath 20. The sheath 20 and the guide wire insertion member 21 can be configured in an integrated fashion with the use of, for example, heat-welding. The guide wire insertion member 21 is provided with a marker M having a radiopaque property. The marker M is configured with a metal coil having a high radiopaque property, such as Pt, Au, or Ir.

The distal portion of the lumen 20a of the sheath 20 is provided with a priming liquid discharge member 22 having a priming liquid discharge hole 22a and through which a priming liquid is discharged. When using the catheter 10, the operator fills the inside of the sheath 20 with the priming liquid so as to reduce the attenuation of ultrasound waves caused by air inside the sheath 20 and to efficiently transmit and receive ultrasound waves. When filling with the priming liquid is performed, a gas such as air retained in the sheath 20 can be discharged from the priming liquid discharge hole 22a formed in the priming liquid discharge member 22 to the outside of the sheath 20.

As illustrated in FIG. 5, a proximal portion 23 of the sheath 20 has an engaged portion 24, which is engageable with an engagement portion 52 of a connection section 50 described below. The engaged portion 24 is configured with a groove receding in a recess shape in the inward radial direction. The engaged portion 24 can be configured integrally with the sheath 20 or can be configured with another member separate from the sheath 20.

The outer diameter d1 of the distal portion of the sheath 20 (the portion which is inserted into the body lumen) is formed to be approximately constant, and the magnitude thereof is not specifically limited but can be formed to be, for example, 3 Fr (French gauge) (about 1 mm). Furthermore, the maximum outer diameter d2 of the proximal portion 23 of the sheath 20 is formed larger than the outer diameter d1 of the distal portion of the sheath 20. This enables forming the engaged portion 24 at the proximal portion 23 of the sheath 20 while keeping the inner diameter of the sheath 20 approximately constant from the distal end to the proximal end. The maximum outer diameter d2 of the proximal portion 23 of the sheath 20 is not specifically limited as long as the magnitude thereof is a size which allows the sheath 20 to be inserted into a guiding catheter G usually used for medical procedures, but can be formed to be 4.5 Fr (about 1.5 mm).

The sheath 20 is formed of a material having flexibility, the material is not limited to a specific material and includes, for example, various thermoplastic elastomers, such as a styrene elastomer, a polyolefin elastomer, a polyurethane elastomer, a polyester elastomer, a polyamide elastomer, a polyimide elastomer, a polybutadiene elastomer, a trans-polyisoprene elastomer, a fluororubber elastomer, and a chlorinated polyethylene elastomer, and a combination of one or two or more (polymer alloy, polymer blend, or laminated body) of these elastomers can also be used as the material. In the present first exemplary embodiment, the sheath 20 has a single-layer structure, but can be configured to have a multi-layered structure. Furthermore, a hydrophilic lubricant coating layer which exhibits lubricating ability at the time of wetting can be arranged on the outer surface of the sheath 20.

As illustrated in FIG. 3(A), the drive shaft 30 includes a pipe body 30*a* having flexibility, and a signal line 30*b* which is inserted through the pipe body 30*a*. The pipe body 30*a* can be configured with, for example, multiple layers of coils having different winding directions around the axis. Examples of the material of the coils include stainless steel and a nickel-titanium (Ni—Ti) alloy. The signal line 30*b* can be configured with, for example, a twisted pair cable or a coaxial cable.

As illustrated in FIG. 3(A), the transmitting and receiving unit 31 includes an ultrasound transducer 31*a*, which transmits and receives ultrasound waves, and a housing 31*b*, which accommodates the ultrasound transducer 31*a*.

The ultrasound transducer 31*a* has the function of transmitting ultrasound waves, which serve as inspection waves, into the body lumen, and receiving ultrasound waves reflected from the body lumen. The ultrasound transducer 31*a* is electrically connected to an electrode terminal 426 (see FIG. 3(B)) via a signal line 30*b*. The ultrasound transducer 31*a* can be formed from a material known as a piezoelectric material. Examples of the material used to configure the ultrasound transducer 31*a* include ceramic and a crystal.

As illustrated in FIG. 1, the operation unit 40 includes a pullback portion 41, which has a nested structure to extend and contract in the axial direction, a hub 42, and a unit connector 43, which interconnects the pullback portion 41 and the hub 42.

The pullback portion 41 includes an outer tube 411, which is fixed to the proximal side of the sheath 20 via the connection section 50, and an inner tube 412, which is fixed to the distal side of the hub 42 and moves relative to the outer tube 411 inside the outer tube 411 in association with the movement of the hub 42.

The hub 42 holds the drive shaft 30 and the inner tube 412. As illustrated in FIG. 3(B), the hub 42 includes a hub main body 421, which has a hollow structure, a priming port 422, which communicates with the inside of the hub main body 421, projections 423*a* and 423*b*, which are used for direction confirmation to confirm the direction of the hub 42 at the time of connection to the external drive apparatus 70, a seal member 424*a*, which seals a portion closer to the proximal side than the priming port 422, a connection pipe 424*b*, which holds the drive shaft 30, a bearing 424*c*, which rotatably supports the connection pipe 424*b*, and a connector portion 425, which is configured to be mechanically and electrically connected to the external drive apparatus 70.

The inner tube 412 is connected to the distal portion of the hub main body 421. The drive shaft 30 is pulled out from the inner tube 412 inside the hub main body 421.

The connection pipe 424*b* is configured to transmit the rotation of a rotor 427 to the drive shaft 30 by holding the drive shaft 30 at the distal end of the connection pipe 424*b*, which is an end portion at the side opposite to the rotor 427. A signal line 30*b* (see FIG. 3(B)) is inserted into the connection pipe 424*b*, and the signal line 30*b* passes through the drive shaft 30 and is then connected to the transmitting and receiving unit 31. A received signal obtained at the transmitting and receiving unit 31 is transmitted to the external drive apparatus 70 and is then subjected to predetermined processing to be displayed as an image.

As illustrated in FIG. 1, the unit connector 43 is fixed to the proximal side of the outer tube 411 and is configured to accommodate the inner tube 412.

The drive shaft 30 passes through the sheath 20, the outer tube 411, and the inner tube 412 and is fixed to the hub 42. The hub 42, the inner tube 412, the drive shaft 30, and the transmitting and receiving unit 31 are connected to each other in such a way as to each move backward and forward in an integrated fashion along the axial direction. When the inner tube 412 is pushed into or pulled out from the unit connector 43 and the outer tube 411, the drive shaft 30 moves forward or backward along the axial direction inside the operation unit 40 and the sheath 20 in conjunction with the inner tube 412.

When an operation for the hub 42 to be pushed toward the distal side is performed, the inner tube 412, which is connected to the hub 42, is pushed into the outer tube 411 and the unit connector 43, so that the drive shaft 30 and the transmitting and receiving unit 31 move toward the distal side inside the sheath 20.

As illustrated in FIG. 4(A), when the inner tube 412 has been pushed into the outer tube 411 toward the distal side to the furthermost extent, the distal portion of the inner tube 412 arrives at the vicinity of the end portion at the distal side of the outer tube 411, i.e., the vicinity of the connection section 50. At this time, the transmitting and receiving unit 31 is located in the vicinity of the distal portion of the sheath 20.

When an operation for the hub 42 to be pulled toward the proximal side is performed, the inner tube 412 is pulled out from the outer tube 411 and the unit connector 43 as indicated by arrow "a1" illustrated in FIG. 1 and FIG. 4(B), so that the drive shaft 30 and the transmitting and receiving unit 31 move toward the proximal side inside the sheath 20 as indicated by arrow "a2".

As illustrated in FIG. 4(B), a stopper 412*a* for coming-off prevention is provided at the distal end of the inner tube 412.

The stopper 412a for coming-off prevention has a function to prevent the inner tube 412 from coming off from the outer tube 411. The stopper 412a for coming-off prevention is configured to get stuck or engage a predetermined position of the inner wall of the unit connector 43 when the hub 42 is fully pulled toward the proximal side, i.e., when the inner tube 412 is pulled out from the outer tube 411 and the unit connector 43 to the maximum extent. Furthermore, to prevent the inner tube 412 from coming off from the outer tube 411, the stopper 412a for coming-off prevention does not necessarily need to be provided, but, for example, the distal end of the inner tube 412 can be processed into such a shape as to prevent coming-off from the outer tube 411, so that the inner tube 412 can be prevented from coming off from the outer tube 411.

As illustrated in FIG. 3(B), a protective tube 61 is fixed to the inner peripheral surface of the distal portion of the inner tube 412 through which the drive shaft 30 passes. The protective tube 61 accommodates the drive shaft 30 therein, and is configured to be slidable along the axial direction inside the outer tube 411 and the sheath 20. In the outer tube 411, since the drive shaft 30 is accommodated in the protective tube 61, when the inner tube 412 moves relative to the outer tube 411, bending of the drive shaft 30 or vibration of the drive shaft 30 occurring during a pullback operation can be prevented or reduced.

Examples of the material used to configure the protective tube 61 include polyimide, blade-containing polyimide, polytetrafluoroethylene (PTFE), polyethylene, and polyamide.

The connection section 50 is configured to be attachable to and detachable from the proximal portion 23 of the sheath 20. As illustrated in FIG. 5, the connection section 50 includes a connector main body portion 51, which is connected to the proximal portion 23 of the sheath 20, an engagement portion 52, which is engageable with the engaged portion 24 of the sheath 20, and a switching portion 53, which switches between the engagement state and the disengagement state.

Furthermore, in the context of the disclosure herein, the term "engagement state" refers to a state in which the engagement portion 52 is engaged with the engaged portion 24 so that the sheath 20 and the connection section 50 are connected to each other as illustrated in FIG. 5, and the term "disengagement state" refers to a state in which the engagement state is removed as illustrated in FIG. 6 so that the connection section 50 can be detached from the sheath 20 as illustrated in FIG. 2.

The distal portion of the connector main body portion 51 is covered by an anti-kink protector 54. Furthermore, a connection portion between the sheath 20 and the connector main body portion 51 is provided with a seal member 55 used to keep a space between the sheath 20 and the operation unit 40 in a liquid-tight manner.

The connector main body portion 51 holds, at the proximal portion thereof, the outer tube 411. As illustrated in FIGS. 8(A) and 8(B), the side surface of the connector main body portion 51 has a slit 511 extending in the axial direction to form a movement pathway of an attachment and detachment lever 532 of the switching portion 53, which is described below.

As illustrated in FIG. 5, FIG. 6, and FIG. 7(A), the engagement portion 52 includes a plurality of engagement claws 521, each of which has a distal end with a shape engageable with the engaged portion 24 of the sheath 20, and an annular member 522, which supports the proximal portion of each engagement claw 521.

The engagement claw 521 is formed from an elastic material which is deformed by being subjected to external force and restores its original shape by being released from external force. As illustrated in FIG. 6 and FIG. 7(A), the engagement claw 521 has a shape curved in such a way as to spread outward in the radial direction toward the distal end when external force is not applied thereto. When in this state, the engagement claw 521 is in the disengagement state, in which the engagement claw 521 is not engaged with the engaged portion 24. As illustrated in FIG. 5, when a holding portion 531 is fitted on the engagement claw 521 to deform the engagement claw 521 inward in the radial direction, the engagement claw 521 enters the engagement state, in which the engagement claw 521 is engaged with the engaged portion 24.

It is desirable that the engagement claws 521 be arranged at regular intervals in the circumferential direction of the annular member 522 as illustrated in FIG. 7(A). The number of engagement claws 521 is not specifically limited, but is four in the present embodiment.

As illustrated in FIG. 5, FIG. 6, and FIG. 7(B), the switching portion 53 includes the holding portion 531, which holds the engagement state by being detachably mounted on the engagement portion 52, and the attachment and detachment lever 532, which is operated to attach or detach the holding portion 531 to or from the engagement portion 52.

The holding portion 531 is a ring-shaped member and is configured to allow the engagement claws 521 to be fitted in the inner hole thereof. When the holding portion 531 is fitted on the engagement claws 521, external force is applied to the engagement claws 521 inward in the radial direction, so that the distal portions of the engagement claws 521 are deformed inward in the radial direction. This causes the engagement state, in which the engagement claws 521 are engaged with the engaged portion 24, as illustrated in FIG. 5.

The attachment and detachment lever 532 is coupled to the proximal side of the holding portion 531. The attachment and detachment lever 532 is configured to be movable within the slit 511 along the axial direction, and the holding portion 531 is configured to be movable backward or forward along the axial direction in association with the backward or forward movement along the axial direction of the attachment and detachment lever 532.

The slit 511 has restriction portions 512, which restrict the movement of the attachment and detachment lever 532 toward the proximal side. In the exemplary embodiment, each restriction portion 512 is configured with a projection (a raised portion) located in such a way as to be able to contact the attachment and detachment lever 532 along the axial direction. Providing the restriction portions 512 prevents the holding portion 531 from coming off from the engagement portion 52 in the event of unintended movement of the attachment and detachment lever 532 toward the proximal side.

The seal member 55 is located in a close contact manner between the outer peripheral surface of the sheath 20 and the connector main body portion 51. This enables keeping a connection portion between the sheath 20 and the connector main body portion 51 in a liquid-tight manner and preventing leakage of physiological saline or body fluid from within the catheter 10. In the exemplary embodiment, the seal member 55 is configured with an O ring, but is not limited to this and can also be configured with, for example, an X ring. Furthermore, the seal member 55 can be buried in a part of the connector main body portion 51 as illustrated in FIG. 5 and FIG. 6, or can be fixed by being sandwiched between the outer peripheral surface of the sheath 20 and the inner peripheral surface of the connector main body portion 51. Examples of the material used to configure the seal member 55 include natural rubber, silicone rubber, nitrile rubber, and fluorine-containing rubber.

Referring back to FIG. 1, the catheter 10 is driven in a state of being connected to the external drive apparatus 70.

As described above, the external drive apparatus 70 is connected to the connector portion 425 (see FIGS. 4(A) and 4(B)) provided at the proximal side of the hub 42.

Furthermore, the external drive apparatus 70 includes a motor 70a, which is a power source to rotate the drive shaft 30, and a motor 70b, which is a power source to move the drive shaft 30 along the axial direction. The rotational motion of the motor 70b is converted into a motion along the axial direction by a ball screw 70c connected to the motor 70b.

The operation of the external drive apparatus 70 is controlled by a control apparatus 71, which is electrically connected to the external drive apparatus 70. The control apparatus 71 includes a central processing unit (CPU) and memory as main constituent components. The control apparatus 71 is electrically connected to a monitor 72.

Next, a usage example of the catheter 10 according to the exemplary embodiment is described with reference to FIGS. 9(A), 9(B), and 9(C) to FIGS. 11(A), 11(B), and 11(C).

Figure 9A:
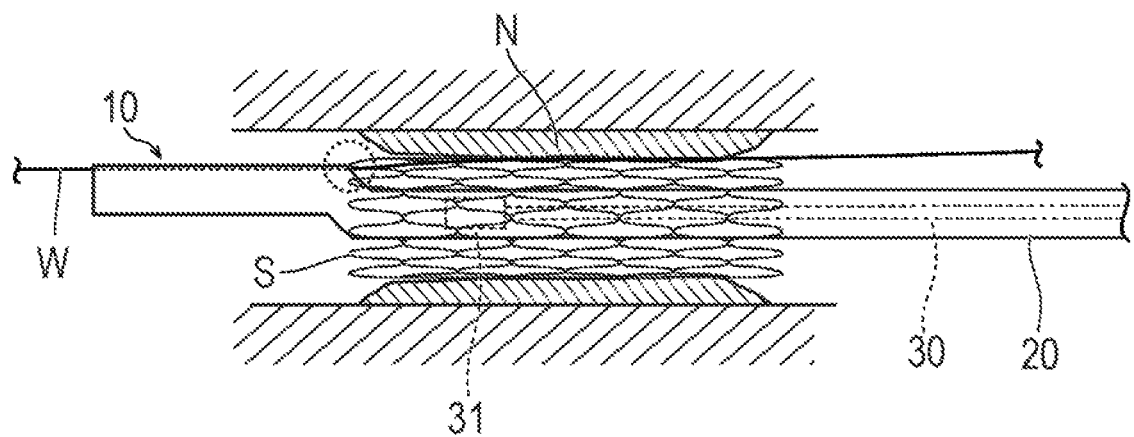
FIGS. 9(A), 9(B), and 9(C) are diagrams illustrating a usage example of the catheter according to the first exemplary embodiment.
Figure 9B:
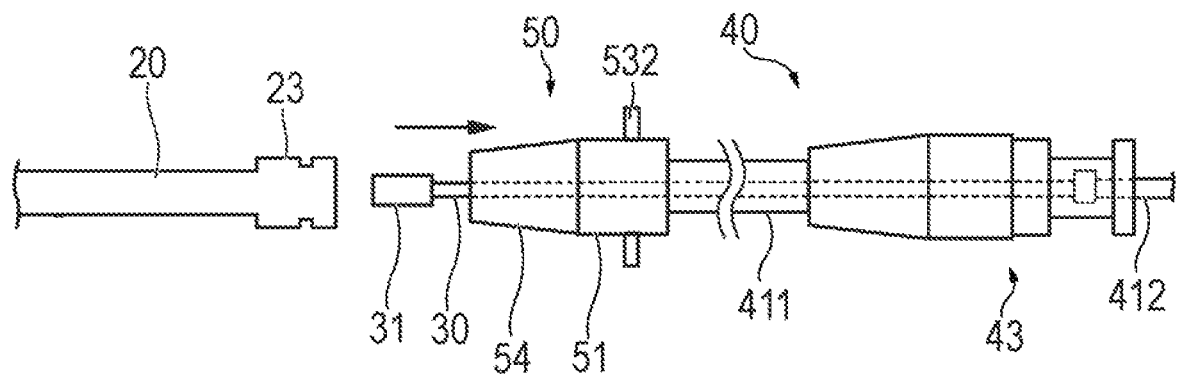
Figure 9C:
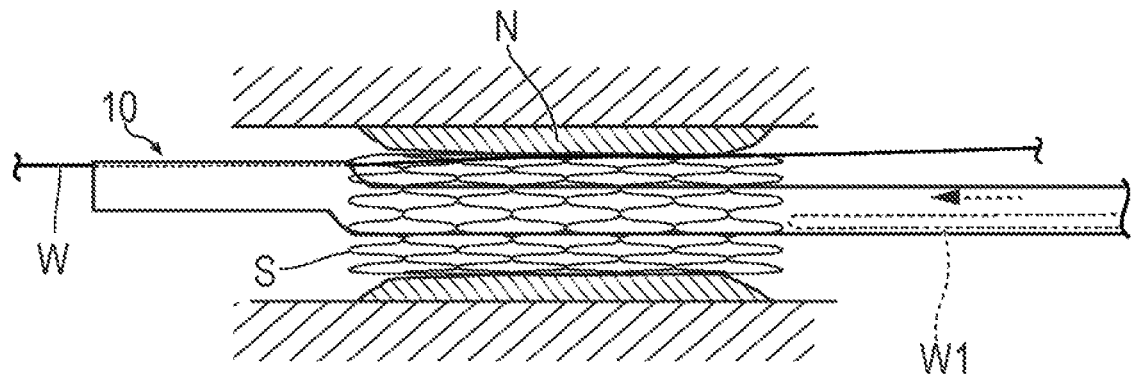
Figure 10A:
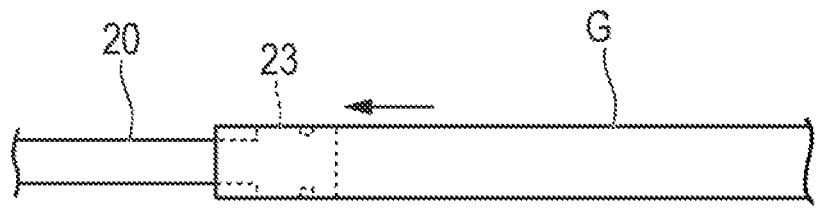
FIGS. 10(A), 10 (B), and 10(C) are diagrams illustrating a usage example of the catheter according to the first exemplary embodiment.
Figure 10B:
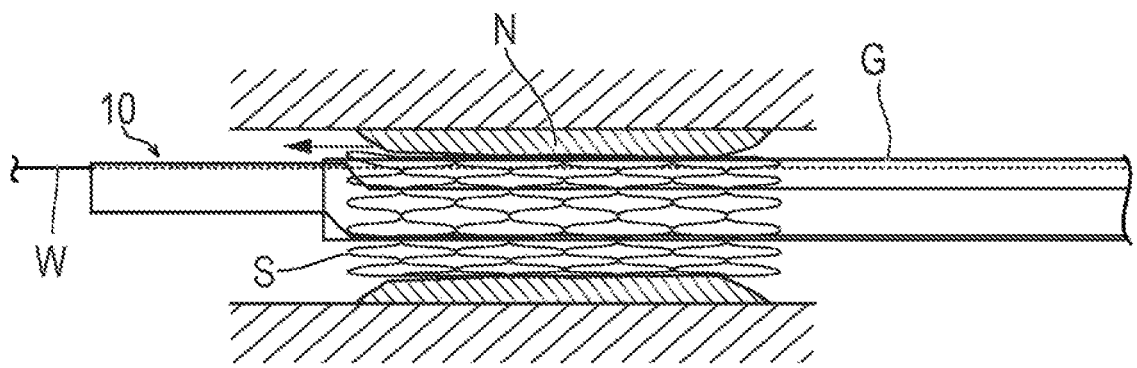
Figure 10C:
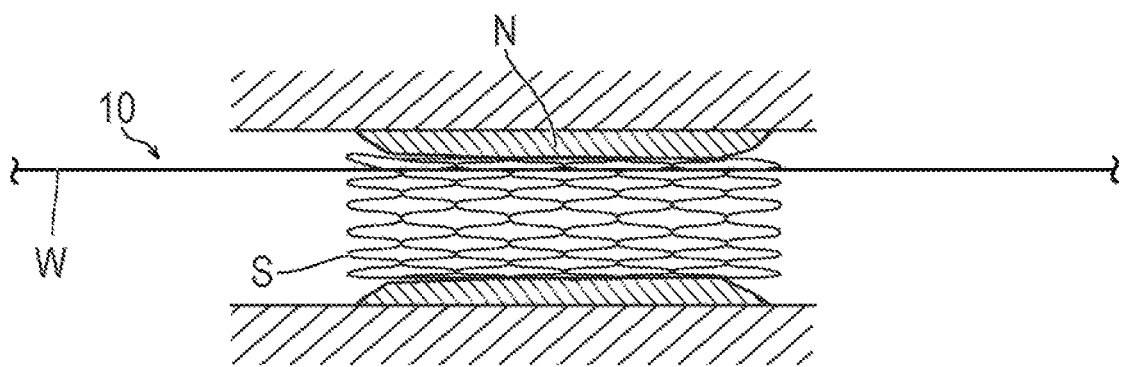
Figure 11A:
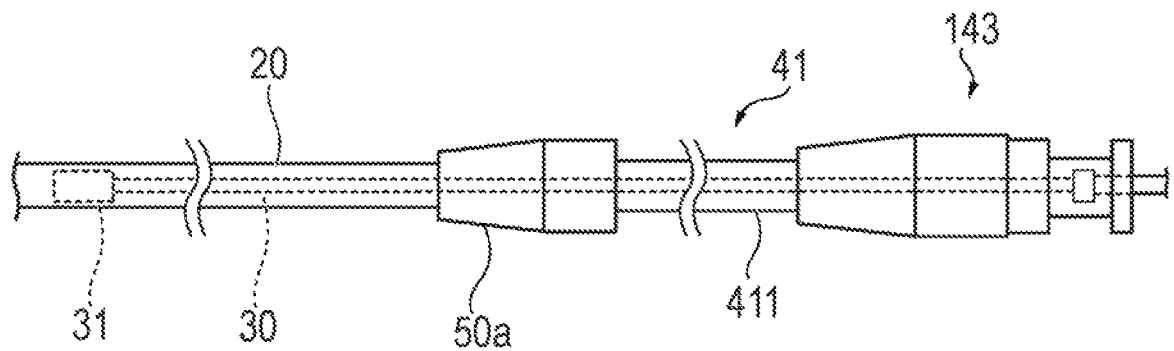
FIGS. 11(A), 11(B), and 11(C) are diagrams illustrating a usage example of a catheter according to a comparative example.
Figure 11B:
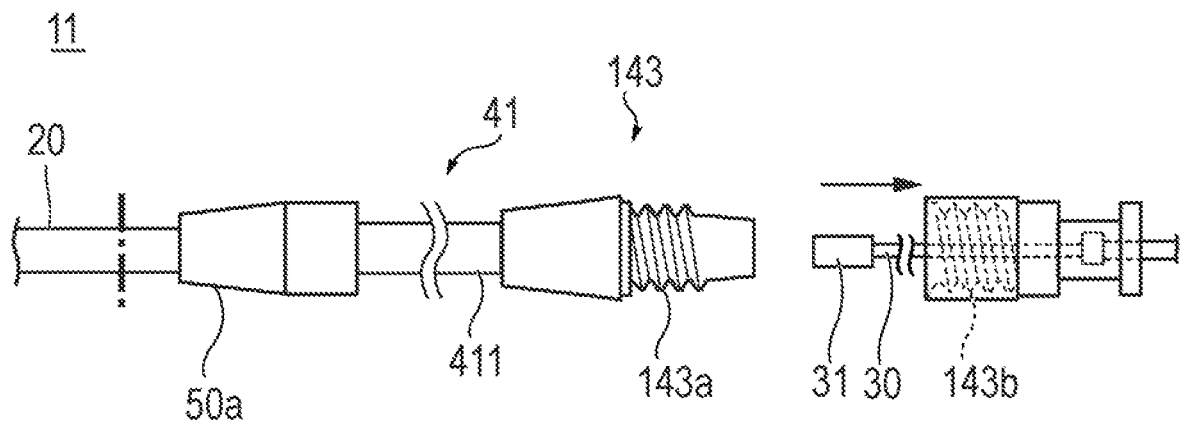
Figure 11C:
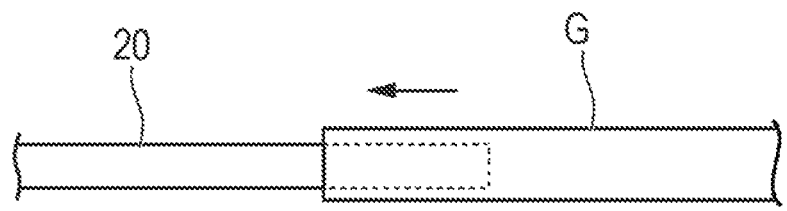

FIGS. 9(A), 9(B), and 9(C) and FIGS. 10(A), 10(B), and 10(C) are diagrams illustrating a usage example of the catheter 10 according to the first exemplary embodiment, and FIGS. 11(A), 11(B), and 11(C) are diagrams illustrating a usage example of a catheter according to a comparative example.

First, the operator prepares the catheter 10 with the connection section 50 connected to the sheath 20. At this time, the engagement portion 52 of the connection section 50 is in the engagement state, in which it is engaged with the engaged portion 24 of the sheath 20 as illustrated in FIG. 5.

Next, the operator performs a priming process to fill the inside of the catheter 10 with physiological saline. Performing the priming process enables removing air inside the catheter 10 and preventing air from entering the body lumen.

In a priming operation, in a state in which the hub 42 is pulled to a maximum extent toward the proximal side (see FIG. 4(B)), for example, a syringe (not illustrated) is connected to the priming port 422 of the hub 42 and physiological saline is then injected into the hub 42. The injected physiological saline passes through the hub 42, the inner tube 412, and the outer tube 411 in turn and then flows to fill up to the inside of the sheath 20 via the connection section 50. In this instance, since a space between the sheath 20 and the connection section 50 is sealed in a liquid-tight manner by the seal member 55, physiological saline or body fluid can be prevented from leaking from inside the catheter 10.

After the priming process, the operator connects the external drive apparatus 70 to the connector portion 425 (see FIGS. 4(A) and 4(B)) of the catheter 10 as illustrated in FIG. 1. Then, the operator pushes the hub 42 inward until the hub 42 abuts on the proximal end of the unit connector 43 (see FIG. 4(A)) to cause the transmitting and receiving unit 31 to move to the distal side as illustrated in FIG. 3(A). In this condition, while the guide wire W is inserted through the guide wire lumen 21a, the sheath 20 is inserted along the guide wire W to an intended position in the body lumen.

To acquire a tomographic image at the intended position in the body lumen, the transmitting and receiving unit 31 moves toward the proximal side while rotating together with the drive shaft 30 (a pullback operation), as illustrated in FIG. 4(B). At this time, the ultrasound transducer 31a of the transmitting and receiving unit 31 transmits and receives ultrasound waves.

The rotation and movement operations of the drive shaft 30 are controlled by the control apparatus 71. The connector portion 425 provided in the hub 42 is rotated in a state of being connected to the external drive apparatus 70, and the drive shaft 30 rotates in conjunction with the rotation of the connector portion 425. The rotational speed of the connector portion 425 and the drive shaft 30 is, for example, 1,800 rpm (revolutions per minute).

The ultrasound transducer 31a transmits ultrasound waves into the body based on a signal sent from the control apparatus 71. A signal corresponding to reflected waves received by the ultrasound transducer 31a is sent to the control apparatus 71 via the drive shaft 30 and the external drive apparatus 70. The control apparatus 71 thus generates a tomographic image of the inside of the body lumen based on a signal sent from the ultrasound transducer 31a, and displays the generated image on the monitor 72.

After acquisition of the tomographic image, the operator performs an operation of extracting the catheter 10 from inside the body lumen. First, the operator pushes the hub 42 inward until the hub 42 abuts on the proximal end of the unit connector 43 (see FIG. 4(A)) to cause the drive shaft 30 to move to the distal side, thus moving the transmitting and receiving unit 31 forward.

In a case where, for example, the catheter 10 is used to confirm a stent S placed at a stenosed site N in the body lumen, as illustrated in FIG. 9(A), an immovable state may occur in which the catheter 10 gets caught by or wedged with a strut of the stent S so that it becomes difficult to extract the catheter 10. Particularly, in the case of a short monorail structure in which the guide wire insertion member 21 is provided at the distal portion of the sheath 20 as in the catheter 10 of the exemplary embodiment, there is provided a step difference (a portion encircled by a dashed line in FIG. 3(A) and FIG. 9(A)) between the proximal end of the guide wire insertion member 21 and the distal portion of the sheath 20. Therefore, the step difference is likely to get caught on, for example, a strut of the stent S, thus causing an immovable state.

In a case where the catheter 10 is immovable, the operator tries to resolve the immovable state by pushing the catheter 10 toward the distal side and rotating the catheter 10. In a case where the immovable state cannot be resolved, the operator tries to correct the immovable state by inserting a balloon catheter or micro-catheter (not illustrated) into the body lumen along the guide wire W.

In a case where the immovable state cannot be corrected even by the above operation, the operator first operates the switching portion 53 to switch from the engagement state illustrated in FIG. 5 to the disengagement state illustrated in FIG. 6. More specifically, in the state in which the attachment and detachment lever 532 is located at the distal side of the slit 511 as illustrated in FIG. 8(A), the operator pulls the attachment and detachment lever 532 toward the proximal side as illustrated in FIG. 8(B). At this time, the attachment and detachment lever 532 passes over the restriction portions 512 and moves to the proximal side of the slit 511. The holding portion 531 moves toward the proximal side according to the movement of the attachment and detachment lever 532. With this, as illustrated in FIG. 6, fitting of the holding portion 531 on the engagement claws 521 is released, so that the engagement claws 521 spread outward in the radial direction. This switches from the engagement state illustrated in FIG. 5 to the disengagement state illustrated in FIG. 6. After switching to the disengagement state, the operator detaches the connection section 50 from the sheath 20 as illustrated in FIG. 9(B). At this time, the operator extracts the drive shaft 30 and the protective tube 61 together with the connection section 50 from the sheath 20.

After extracting the drive shaft 30, as illustrated in FIG. 9(C), the operator tries to resolve the immovable state by inserting a guide wire W1 (higher in rigidity than the drive shaft 30) instead of the drive shaft 30 in order to improve the operability of the distal portion of the catheter 10.

In a case where the immovable state cannot be resolved even by the above operation, as illustrated in FIG. 10(A), the operator inserts a guiding catheter G into the body lumen while causing the sheath 20 to be inserted into the guiding catheter G in such a way as to overlay the guiding catheter G on the sheath 20. As illustrated in FIG. 10(B), the operator resolves the immovable state by inserting the guiding catheter G up to a portion at which the immovable state occurs in the distal portion of the sheath 20 (a portion encircled by a dashed line illustrated in FIG. 9(A)). Furthermore, the guide wire W1 can be kept inserted through the sheath 20 or can be temporarily extracted.

Furthermore, in the exemplary embodiment, a guiding catheter G having an inner diameter larger than the maximum outer diameter d2 of the proximal portion 23 of the sheath 20 is used. For example, in a case where the maximum outer diameter d2 of the proximal portion 23 of the sheath 20 is 4.5 Fr, a guiding catheter G with an inner diameter of 5 Fr (about 1.67 mm) can be used. This enables the sheath 20 to be inserted into the guiding catheter G.

After correcting the immovable state, as illustrated in FIG. 10(C), the operator extracts the catheter 10 and the guiding catheter G from inside the body lumen.

FIG. 11(A) illustrates a catheter 11 according to a comparative example. In the catheter 11 according to the comparative example, as illustrated in FIG. 11(B), a unit connector 143 located closer to the proximal side than the pullback portion 41 includes a male screw portion 143a and a female screw portion 143b, which are able to be screwed with each other, and the distal portion and the proximal portion of the unit connector 143 can be connected to each other or separated from each other by screwing or unscrewing the male screw portion 143a and the female screw portion 143b with or from each other.

Separating the unit connector 143 enables extracting the drive shaft 30 from inside the catheter 11, as illustrated in FIG. 11(B). In a state in which the unit connector 143 is separated, a connection section 50a, the outer tube 411, which is a part of the operation unit 40, and the male screw portion 143a of the unit connector 143 are in a state of being coupled to the sheath 20. Since, usually, the outer diameter of the unit connector 143 is larger than the inner diameter of the guiding catheter G, it is impossible to overlay the guiding catheter G on the unit connector 143. Therefore, if a procedure of inserting the sheath 20 through into the guiding catheter G and inserting the guiding catheter G into the body lumen is performed, to separate the connection section 50a, the outer tube 411, the male screw portion 143a of the unit connector 143 from the sheath 20, an operation of preparing a cutting tool, such as a skin cut scalpel, and cutting off the proximal portion of the sheath 20 (a dashed-dotted line portion illustrated in FIG. 11(B)) would be required. With this, an operation of resolving the immovable state may become complicated. Furthermore, in a case where, to remove the immovable state, the guide wire W1 is inserted into the sheath 20 instead of the drive shaft 30, unless the guide wire W1 is extracted before the proximal portion of the sheath 20 is cut off, the guide wire W1 would be left in the sheath 20 and become unable to be extracted. With this, an operation of, for example, replacing or shaping the guide wire W1 would become unable to be performed. Therefore, an operation of temporarily extracting the guide wire W1 before cutting-off of the sheath 20 and re-inserting the guide wire W1 into the sheath 20 after cutting-off of the sheath 20 becomes required. With this, a time required for the procedure would become long.

Furthermore, the sheath 20 has a small wall thickness and, therefore, may be damaged if being reused, and, since the sheath 20 is inserted into the body lumen and directly contacts a body fluid, from a hygiene viewpoint, the sheath 20 cannot be reused. In the above-mentioned procedure, since a part of the operation unit is also separated together with the sheath 20, the operation unit also cannot be reused. Therefore, the whole catheter 11 is required to be made disposable, thus causing a decrease in medical economic performance.

On the other hand, in the catheter 10 according to the exemplary embodiment, the sheath 20 can be separated from the connection section 50 and the operation unit 40 by detaching the connection section 50 from the sheath 20. With this, since only the sheath 20 is left in the living body, a procedure of inserting sheath 20 through the guiding catheter G and inserting the guiding catheter G into the body lumen can be performed without cutting off the proximal portion 23 of the sheath 20. A time required to prepare a cutting tool, such as a skin cut scalpel, is cut down, and an operation time can be shortened by replacing a time required to cut off the sheath 20 with an operation of disconnecting the connection section 50. Since the time for the procedure is shortened, the physical load on patients can be reduced. Furthermore, in the catheter 10 according to the exemplary embodiment, in a case where, to remove the stuck state, the guide wire W1 is inserted into the sheath 20 instead of the drive shaft 30, an operation of temporarily extracting the guide wire W1 and then re-inserting the guide wire W1 also becomes unnecessary, so that the time for the procedure can be further reduced.

Furthermore, since the sheath 20, which is inserted into the body lumen and directly contacts a body fluid, can be separated from the connection section 50 and the operation unit 40, which are not inserted into the body lumen, only the sheath 20 can be made disposable. The drive shaft 30, the connection section 50, and the operation unit 40 can be reused after being subjected to appropriate treatments, such as sterilization and disinfection. This reduces components to be disposed of and, therefore, enables improving medical economic performance.

As described above, the catheter 10 according to the exemplary embodiment includes the sheath 20 configured to be inserted into a body lumen, the drive shaft 30 configured to be inserted into the sheath 20 and to transmit mechanical drive force, the operation unit 40 configured to operate the drive shaft 30, and the connection section 50 having a proximal side connected to the operation unit 40 and a distal side connected to the sheath 20 in such a way as to be attachable to and detachable from the sheath 20.

According to the above-described catheter 10, when the catheter 10 gets stuck or lodged in the body lumen, detaching the connection section 50 from the sheath 20 enables separating the sheath 20 from the connection section 50 and the operation unit 40. This enables performing an operation which improves the operability of a distal portion of the sheath 20 by extracting the drive shaft 30 from inside the sheath 20 and, instead, inserting a guide wire which is higher in rigidity than the drive shaft 30 and then resolves the immovable or lodged state. Furthermore, separating the sheath 20 from the connection section 50 and the operation unit 40 causes only the sheath 20 to remain in the living body and, therefore, enables promptly performing an operation which resolves the immovable state by inserting a guiding catheter G into the body lumen while causing the sheath 20 to be inserted through into the guiding catheter G without cutting off the proximal portion 23 of the sheath 20. Moreover, since the sheath 20, which is inserted into the body lumen and directly contacts a body fluid, can be separated from the connection section 50 and the operation unit 40, which are not inserted into the body lumen, only the sheath 20 can be made disposable and the drive shaft 30, the connection section 50, and the operation unit 40 can be reused after being subjected to appropriate treatments, such as sterilization and disinfection. This reduces components to be disposed of in the catheter 10 and, therefore, enables improving medical economic performance.

Furthermore, the sheath 20 includes the engaged portion 24, and the connection section 50 includes the engagement portion 52, which is engageable with the engaged portion 24 of the sheath 20. With this, the connection section 50 can be relatively easily connected to the sheath 20 by engaging the engagement portion 52 with the engaged portion 24.

Moreover, the connection section 50 further includes the switching portion 53, which switches between the engagement state, in which the engagement portion 52 is engaged with the engaged portion 24, and the disengagement state, in which the engagement state is removed. This enables the operator to relatively easily attach and detach the connection section 50 to and from the sheath 20 by operating the switching portion 53. With this, the trouble and time required for the procedure can be shortened, and a psychological load on the operator in an emergency situation in which the catheter 10 is stuck or immovable can be reduced. Additionally, since the time required for the procedure is shortened, a less-invasive procedure can be performed.

Furthermore, the connection section 50 further includes the holding portion 531 configured to hold the engagement state, in which the engagement portion 52 is engaged with the engaged portion 24. With this, when the catheter 10 is used, the engagement state can be prevented from being inadvertently removed, so that the state of the connection section 50 being connected to the sheath 20 can be maintained.

Moreover, the connection section 50 further includes the seal member 55 configured to keep a space between the sheath 20 and the connection section 50 in a liquid-tight manner in a state of being connected to the sheath 20. This enables preventing leakage of physiological saline or body fluid from within the catheter 10.

Next, a modified example of the first exemplary embodiment is described with reference to FIG. 12. Furthermore, similar components to those of the above-described first exemplary embodiment are assigned the respective same reference numerals, and the description thereof is omitted. Moreover, portions not specifically mentioned in the modified example are assumed to be able to be configured in the same manner as in the above-described first exemplary embodiment.

Figure 12:
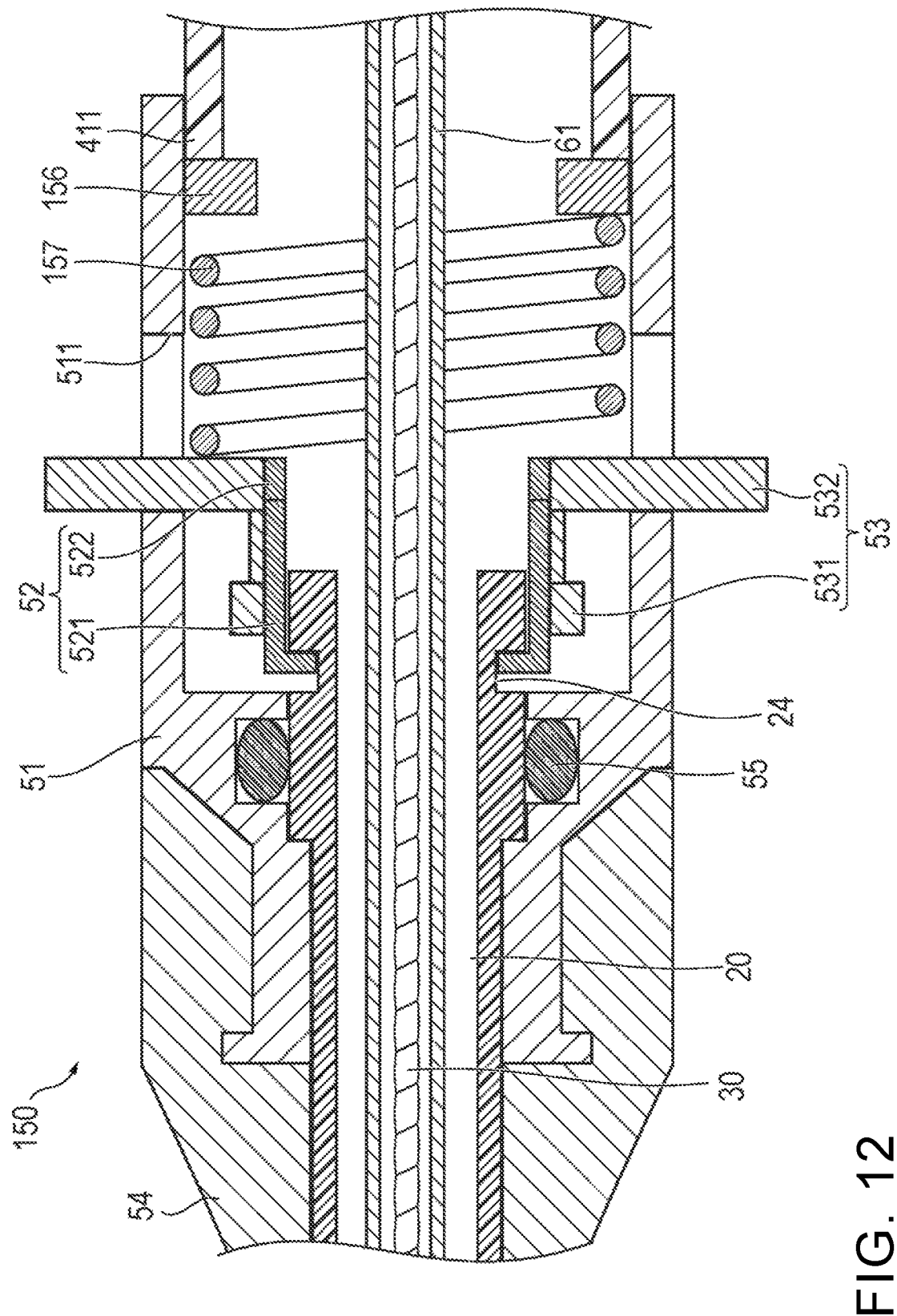
FIG. 12 is an enlarged sectional view illustrating a configuration of a portion near a connection section of a catheter according to a modified example of the disclosure.

FIG. 12 is an enlarged sectional view illustrating a configuration of the vicinity of a connection section 150 in a catheter according to the modified example.

The modified example differs from the above-described first exemplary embodiment in that the connection section 150 further includes a latch member 156, which is fixed to the proximal side of the connector main body portion 51, and an elastic member 157, which is provided between the latch member 156 and the attachment and detachment lever 532.

The elastic member 157 is configured with, for example, a coil spring and urges the attachment and detachment lever 532 toward the distal side. This enables the engagement state to be stably maintained between the engaged portion 24 and the engagement portion 52. Moreover, when the attachment and detachment lever 532 is moved toward the proximal side, since the elastic member 157 is compressed in the axial direction, the disengagement state can be set.

Even in the catheter according to the modified example, an effect similar to that in the above-described first exemplary embodiment can be exerted.

Next, a second exemplary embodiment is described with reference to FIG. 13 and FIG. 14. Furthermore, similar components to those of the above-described first exemplary embodiment are assigned the respective same reference numerals, and the description thereof is omitted. Moreover, portions not specifically mentioned in the second exemplary embodiment are assumed to be able to be configured in the same manner as in the above-described first exemplary embodiment.

Figure 13:
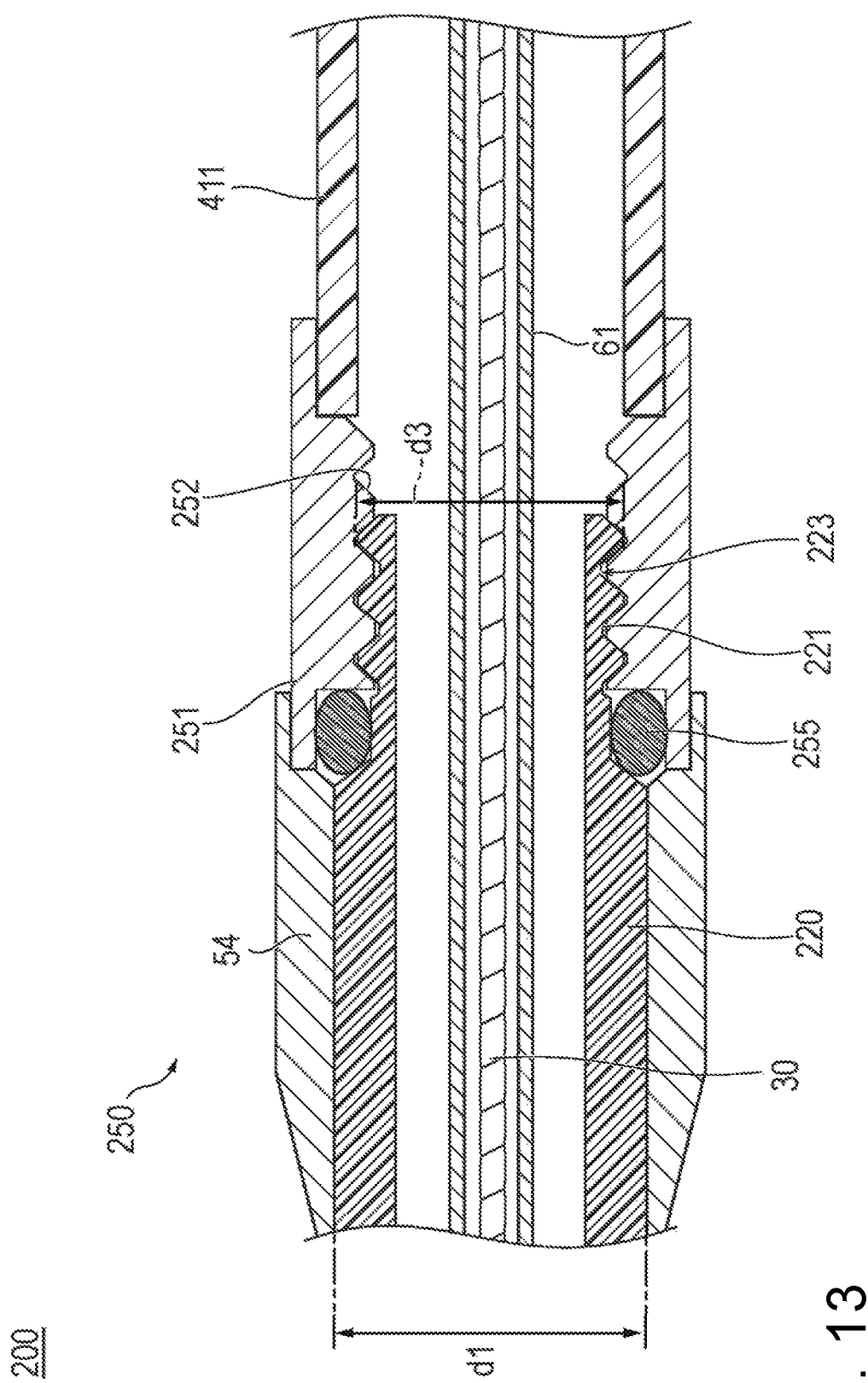
FIG. 13 is an enlarged sectional view illustrating a configuration of a portion near a connection section of a catheter according to a second exemplary embodiment of the disclosure.
Figure 14:
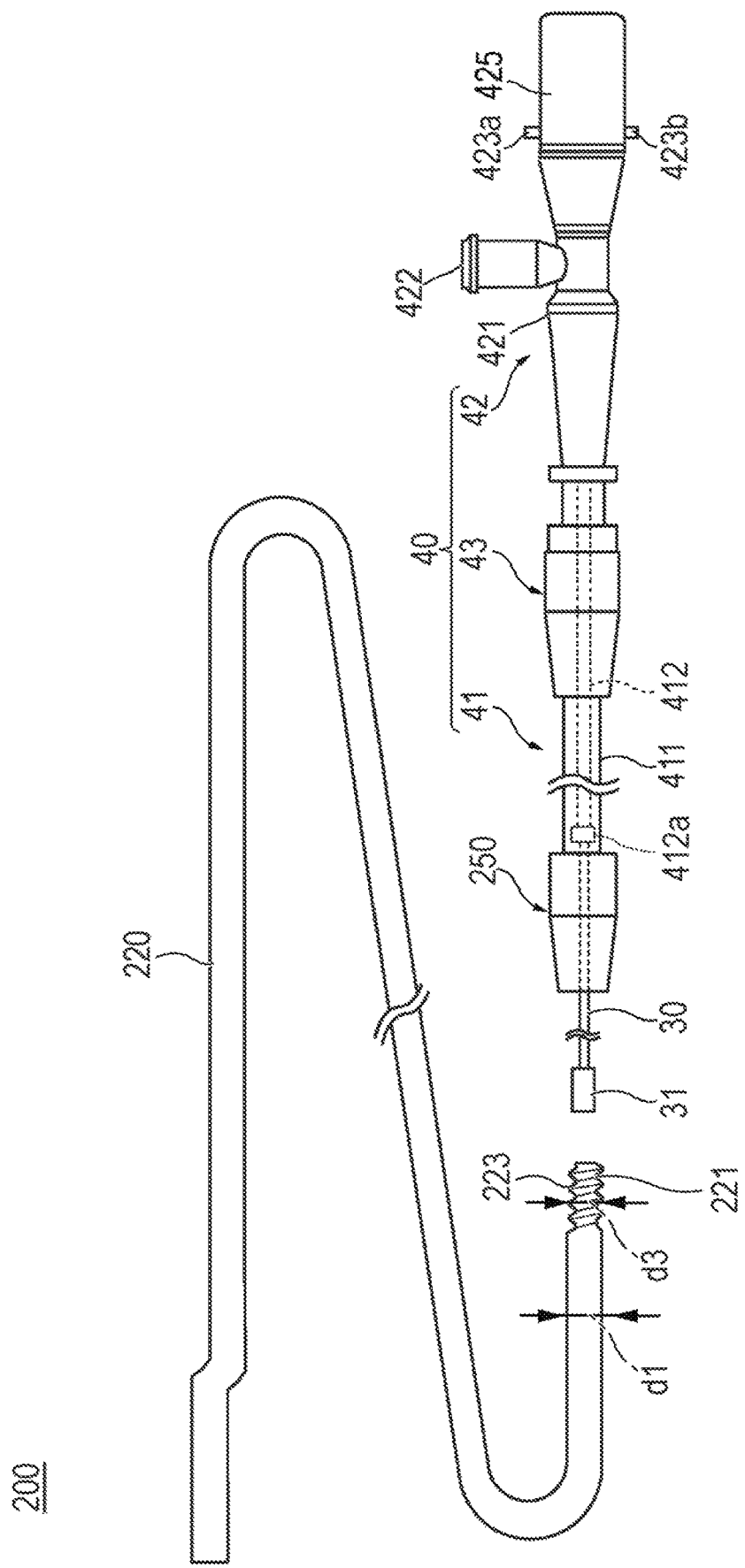
FIG. 14 is a plan view illustrating a state in which the connection section of the catheter according to the second exemplary embodiment is detached from a sheath.

FIG. 13 is an enlarged sectional view illustrating a configuration of the vicinity of a connection section 250 of a catheter 200 according to the second exemplary embodiment, and FIG. 14 is a plan view illustrating a state in which the connection section 250 of the catheter 200 is detached from a sheath 220. Furthermore, an overall view of the catheter 200 with the connection section 250 connected to the sheath 220 is similar to that of the above-described first exemplary embodiment illustrated in FIG. 1, and is, therefore, omitted from illustration.

The second exemplary embodiment differs from the above-described first exemplary embodiment in that the catheter 200 has a screw structure in which a proximal portion 223 of the sheath 220 and the connection section 250 are able to be screwed with and unscrewed from each other.

As illustrated in FIG. 13, the proximal portion 223 of the sheath 220 has a male screw portion (corresponding to a first screw portion) 221 formed on a part of the outer peripheral surface thereof. The maximum outer diameter d3 of the proximal portion 223 of the sheath 220 is formed in such a way as to be smaller than the outer diameter d1 of the distal portion of the sheath 220. Furthermore, the outer diameter d1 of the distal portion of the sheath 220 can be configured in the same manner as that in the above-described first embodiment.

The connection section 250 includes a connector main body portion 251, a female screw portion (corresponding to a second screw portion) 252 formed on a part of the inner peripheral surface of the connector main body portion 251, and a seal member (O ring) 255. Furthermore, as in the above-described first exemplary embodiment, the distal portion of the connector main body portion 251 is covered by an anti-kink protector 54.

The female screw portion 252 is configured to be able to be screwed with the male screw portion 221 of the sheath 220. The connection section 250 is connected to the sheath 220 by causing the male screw portion 221 of the sheath 220 to be screwed with (fitted in) the female screw portion 252 of the connection section 250. Moreover, as illustrated in FIG. 14, the connection section 250 can be detached from the sheath 220 by disconnecting the connection section 250 from the sheath 220 with unscrewing.

The seal member 255 is located closer to the distal side than the female screw portion 252, and keeps a space between the sheath 220 and the connection section 250 in a liquid-tight manner in a state of being connected to the sheath 220. The seal member 255 can be buried in a part of the connector main body portion 251, or can be fixed by being sandwiched between the outer peripheral surface of the sheath 220 and the inner peripheral surface of the connector main body portion 251. The configuration of the seal member 255 is substantially similar to that of the seal member 55 of the catheter 10 according to the above-described first exemplary embodiment.

Usually, in a state in which the connection section 250 is connected to the sheath 220 by causing the male screw portion 221 of the sheath 220 to be screwed with (fitted in) the female screw portion 252 of the connection section 250, since a connection portion thereof is formed by mechanical joining, sealing performance (air tightness and liquid tightness) is low. Therefore, when a priming process is being performed or when the catheter 200 is inserted into the body lumen, leakage of physiological saline or body fluid from the connection portion may occur.

Arranging the seal member 255 as in the second exemplary embodiment enables keeping the connection portion between the sheath 220 and the connection section 250 in a liquid-tight manner to prevent leakage of physiological saline or body fluid from inside the catheter 200.

Furthermore, when, during the priming process, a priming liquid is caused to flow from the proximal side to the distal side, pressure is exerted on the seal member 255 in the axial direction. At this time, since the seal member 255 is located closer to the distal side than a portion at which the male screw portion 221 of the sheath 220 and the female screw portion 252 are screwed with each other, pressure exerted from the priming liquid is restrained at the proximal side, so that deformation of the seal member 255 can be prevented or reduced. Moreover, in a screw structure portion in which the male screw portion 221 and the female screw portion 252 are screwed with each other, since the flow path of the priming liquid is complicated and a clearance (gap) through which the priming liquid is allowed to pass is small, pressure loss occurs, so that pressure exerted on the seal member 255 can be reduced. This enables keeping the sealing performance of the seal member 255 at the connection portion between the sheath 220 and the connector main body portion 251.

Even in the catheter according to the second exemplary embodiment, as in the above-described first exemplary embodiment, when the catheter is stuck or wedged in the body lumen, detaching the connection section 250 from the sheath 220 by unscrewing the male screw portion 221 from the female screw portion 252 enables relatively easily separating the sheath 220 from the connection section 250 and the operation unit 40, as illustrated in FIG. 14. This enables performing an operation which improves the operability of a distal portion of the sheath 220 by extracting the drive shaft 30 from inside the sheath 220 and, instead, inserting a guide wire which is higher in rigidity than the drive shaft 30 and then removes the stuck state. Furthermore, separating the sheath 220 from the connection section 250 and the operation unit 40 causes only the sheath 220 to remain in the living body and, therefore, enables promptly performing an operation which resolves the immovable state by inserting a guiding catheter G into the body lumen while causing the sheath 220 to be inserted through into the guiding catheter G without cutting off the proximal portion 223 of the sheath 220.

Moreover, the sheath 220, which is inserted into the body lumen and directly contacts a body fluid, can be separated from the connection section 250 and the operation unit 40, which are not inserted into the body lumen, only the sheath 220 can be made disposable and the drive shaft 30, the connection section 250, and the operation unit 40 can be reused after being subjected to appropriate treatments, such as sterilization and disinfection. This reduces components to be disposed of in the catheter 200 and, therefore, enables improving medical economic performance.

In the catheter according to the second exemplary embodiment, the sheath 220 includes the male screw portion (first screw portion) 221, and the connection section 250 includes the female screw portion (second screw portion) 252, which is able to be screwed with the male screw portion 221. This enables relatively easily attaching and detaching the connection section 250 to and from the sheath 220 by using a screw structure.

While the catheters according to the disclosure herein have been described above via the embodiments and modification example, the invention is not limited to the configurations described in the exemplary embodiments, but can be modified or altered as appropriate based on the description of claims.

For example, while, in the above-described exemplary embodiments, a case in which the invention is applied to a diagnostic imaging catheter for use in intravascular ultrasound (IVUS) has been described, the disclosure is not specifically limited to this but can be applied to every type of catheter as long as it is the type in which a drive shaft that performs mechanical driving is included in a sheath. The diagnostic imaging catheter to which the invention can be applied includes, for example, a diagnostic imaging catheter using light for use in optical coherence tomography (OCT) or optical frequency domain imaging (OFDI) and a hybrid-type (dual-type) diagnostic imaging catheter usable in both intravascular ultrasound and optical coherence tomography. Furthermore, the disclosure can be applied to not only the diagnostic imaging catheter but also a catheter for use in an endoscopic system or directional coronary atherectomy (DCA).

Moreover, the configuration of the connection section is not limited to those described in the above-described exemplary embodiments and modified example as long as it is attachable to and detachable from the sheath.

What is claimed is:

1. A catheter comprising:
   an axially extending sheath configured to be inserted into a body lumen, the sheath including an engaged portion;
   an axially extending drive shaft configured to be inserted into the sheath and to transmit mechanical drive force;
   an operation unit configured to operate the drive shaft;
   a connection section having a proximal side connected to the operation unit and a distal side connected to the sheath in such a way as to be attachable to and detachable from the sheath;
   the connection section including a connector main body portion, the connector main body portion including a distal portion surrounding an axially extending part of the sheath, the connector main body portion also including an axially extending slit;
   the connection section including an engagement portion comprised of plural circumferentially spaced-apart engagement parts that are in an engagement state in which each of the engagement parts is engaged with the engaged portion of the sheath so that the connection section is connected to the sheath, the engagement portion also comprising a support part that is connected to and supports each of the engagement parts, the engagement parts being movable from the engagement state to a disengagement state in which the engagement parts are out of engagement with the engaged portion of the sheath to permit the connection section to be disconnected from the sheath; and the connection section including a switching portion comprised of a holding part surrounding an axially extending portion of the circumferentially spaced-apart engagement parts to hold the engagement parts it the engagement state in which the engagement parts are engaged with the engaged portion of the sheath, the holding part being axially movable in a proximal direction relative to both the connector main body portion and the engagement parts to move form the engagement state to a disengagement state in which the holding part is positioned proximal of said axially extending portion of the plural engagement parts and the engagement parts automatically move out of engagement with the engaged portion of the sheath to permit the connection section to be disconnected from the sheath, the switching portion also comprising a lever connected to the holding part so that movement of the lever results in movement of the holding part, the lever passing through the axially extending slit and being movable in the proximal direction relative to the connector main body portion and along the axially extending slit to move the holding part from the engagement state to the disengagement state.

2. The catheter according to claim 1, wherein the engaged portion of the sheath includes a groove in an outer surface of the sheath, and wherein each of the engagement parts of the connection section includes an inwardly projecting projection that is positioned in the groove in the outer surface of the sheath.

3. The catheter according to claim 2, wherein each of the plurality of engagement parts is formed from an elastic material.

4. The catheter according to claim 3, wherein the engagement parts each curve outwardly away from a central axis of the engagement part before the engagement parts are surrounded by holding part, the holding part surrounding the axially extending portion of the plural circumferentially spaced-apart engagement parts deforming each of the plural engagement parts inward in a radial direction such that the inwardly projecting projection at of each of the engagement parts remains positioned in and engaged with the groove in the outer surface of the sheath, thereby holding the engagement state.

5. The catheter according to claim 4, wherein the lever is coupled to a proximal side of the holding part.

6. The catheter according to claim 1, wherein the engaged portion of the sheath includes a groove in an outer surface of the sheath, and each of the engagement parts of the connection section includes a distal end at which is located an inwardly projecting claw positioned in the groove in the outer surface of the sheath.

7. The catheter according to claim 6, wherein the holding part holds the inwardly projecting claw of each of the engagement parts in the groove in the outer surface of the sheath so that the claws are unable to move out of the groove.

8. The catheter according to claim 1, wherein the connector main body portion is connected to a proximal portion of the sheath, and a seal member is positioned between an inner surface of the connector main body and an outer surface of the sheath to keep a space between the sheath and the connection section in a liquid-tight manner in a state of being connected to the sheath.

9. The catheter according to claim 1, wherein a distal portion of the connection section is covered by an anti-kink protector.

10. The catheter according to claim 1, wherein a proximal portion of the connector main body surrounds a proximal portion of the sheath, the proximal portion of the connector main body portion that surrounds the proximal portion of the sheath including an inner surface facing towards an outer surface of the proximal portion of the sheath, the holding part of the switching portion being positioned between the inner surface of the proximal portion of the connector main body portion and the outer surface of the of the proximal portion of the sheath.

11. The catheter according to 1, wherein the holding part is an annular holding part, the slit is a first slit and the lever is a first lever, the connector main body portion also comprising a second axially extending slit, the switching portion of the connection section also comprising a second lever connected to the holding part so that movement of the second lever results in movement of the holding part, the second lever passing through the second axially extending slit and being movable in the proximal direction relative to the connector main body portion and along the axially extending second slit to move the holding part from the engagement state to the disengagement state.

12. A catheter comprising:

a sheath configured to be inserted into a body lumen and possessing an outwardly facing outer surface;

a connection section having a proximal side configured to be connected to an operation unit and a distal side detachably connected to the sheath;

the sheath including an engaged portion;

the connection section including a connector main body portion surrounding a portion of the sheath, the connector main body portion including a proximal portion possessing an inner surface, the proximal portion of the connector main body portion surrounding an axially extending part of the sheath, the inner surface of the proximal portion of the connector main body portion facing towards the outer surface of the axially extending part of the sheath, the inner surface of the proximal portion of the connector main body portion being spaced from the outer surface of the axially extending part of the sheath so that a space exists between the inner surface of the proximal portion of the connector main body portion and the outer surface of the axially extending part of the sheath the connection section including an engagement portion comprised of plural circumferentially spaced-apart engagement parts that are in an engagement state in which each of the engagements parts is engaged with the engaged portion of the sheath to connect the connection section and the sheath;

a holding part that surrounds an axially extending portion of each of the engagement parts to hold the engagement parts in engagement with the engaged portion of the sheath and prevent the engagement parts from being disengaged from the engagement portion of the sheath so that the connection section remains connected to the sheath; and the holding part being positioned in the space between the inner surface of the proximal portion of the connector main body portion and the outer surface of the axially extending part of the sheath, the holding part possessing an outer surface facing towards and spaced form the inner surface of the proximal portion of the connector main body portion, the holding part being axially moveable relative to both the engagement parts and the connector main body portion to a position that allows the engagement parts to move out of engagement with the engaged portion of the sheath so that the connection section is disconnectable from the sheath.

13. The catheter according to claim 12, wherein the engaged portion of the sheath includes a groove in the outer surface of the sheath.

14. The catheter according to claim 13, wherein the engagement parts are engagement claws circumferentially spaced apart from one another and fixed to an annular member, the plurality of engagement claws projecting axially away from the annular member in a distal direction.

15. The catheter according to claim 14, wherein the holding part is a ring-shaped member that encircles the engagement claws and holds distal ends of each of the engagement claws in the groove in the outer surface of the sheath.

16. The catheter according to claim 14, further comprising an axially moveable attachment and detachment lever coupled to a proximal side of the holding part so that axial movement of the attachment and detachment lever results in axial movement of the holding part.

17. The catheter according to claim 16, wherein the connector main body portion includes a slit extending in an axial direction and defining a movement pathway for the attachment and detachment lever, the attachment and detachment lever passing through the slit so that a distal end of the attachment and detachment lever is positioned outside the connector main body portion.

18. A catheter comprising:
a sheath configured to a body lumen and possessing an outwardly facing outer surface;
a connection section having a proximal side configured to be connected to an operation unit and a distal side detachably connected to a proximal portion of the sheath;
the sheath including an engaged portion;
the connection section including a connector main body possessing an interior in which is located the proximal portion of the sheath, the connector main body portion including a proximal portion possessing an inner surface, the proximal portion of the connector main body portion surrounding an axially extending part of the sheath, the inner surface of the proximal portion of the connector main body portion facing toward the outer surface of the axially extending part of the sheath, the inner surface of the proximal portion of the connector main body portion being space from the outer surface of the axially extending part of the sheath so that a space exists between the inner surface of the proximal portion of the connector main body portion and the outer surface of the axially extending part of the sheath,
the connection section also including at least one claw positioned in the space between the inner surface of the proximal portion of the connector main body portion and the outer surface of the axially extending part of the sheath, the at least one claw being in engagement with the engaged portion of the sheath so that the connection section is connected to the sheath;
an axially movable holding part located in a first position in which the holding part encircles an axially extending portion of the at least one claw and holds the at least one claw in engagement with the engaged portion of the sheath in a manner that prevents the at least one claw from being disengaged from the engaged portion of the sheath thereby preventing the connection section from being disconnected from the sheath; and
the holding part being axially movable relative to both the at least one claw and the connector main body portion from the first position to a second position in which the holding part no longer encircles said axially extending portion of the at least one claw, the at least one claw being configured to automatically expand outward when the holding part is axially moved to the second position so that the at least one claw moves out of engagement with the engaged portion of the sheath thereby disconnecting the connection section from the sheath, the at least one claw moving out of engagement with the engaged portion of the sheath without any axial movement of the connector main body portion relative to the at least one claw.

19. The catheter according to claim 18, wherein the at least one claw includes plural claws that each project axially from an annular member and that are circumferentially spaced apart from one another, the holding part in the first position encircling all of the plural claws to hold the plural claws in engagement with the engaged portion of the sheath.

* * * * *